(12) United States Patent
McFetridge

(10) Patent No.: US 9,599,604 B2
(45) Date of Patent: Mar. 21, 2017

(54) FLOW CHAMBERS, METHODS OF USING THE FLOW CHAMBER, AND METHODS OF MAKING THE FLOW CHAMBER

(71) Applicant: University of Florida Research Foundation, Incorporated, Gainesville, FL (US)

(72) Inventor: Peter S. McFetridge, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 9 days.

(21) Appl. No.: 14/281,186

(22) PCT Filed: Dec. 7, 2012

(86) PCT No.: PCT/US2012/068387
§ 371 (c)(1),
(2) Date: May 19, 2014

(87) PCT Pub. No.: WO2013/086284
PCT Pub. Date: Jun. 13, 2013

(65) Prior Publication Data
US 2014/0287451 A1    Sep. 25, 2014

Related U.S. Application Data

(60) Provisional application No. 61/568,740, filed on Dec. 9, 2011.

(51) Int. Cl.
| | | |
|---|---|---|
| C12M 1/00 | (2006.01) | |
| G01N 33/50 | (2006.01) | |
| C12M 1/12 | (2006.01) | |
| C12M 3/00 | (2006.01) | |
| C12M 1/18 | (2006.01) | |
| C12M 1/34 | (2006.01) | |
| C12M 3/06 | (2006.01) | |

(52) U.S. Cl.
CPC .......... *G01N 33/5005* (2013.01); *C12M 1/18* (2013.01); *C12M 1/34* (2013.01); *C12M 23/16* (2013.01); *C12M 23/22* (2013.01); *C12M 23/34* (2013.01); *C12M 23/42* (2013.01); *C12M 23/46* (2013.01); *C12M 25/00* (2013.01); *C12M 25/02* (2013.01); *C12M 25/04* (2013.01); *C12M 25/14* (2013.01); *C12M 29/10* (2013.01); *C12M 41/36* (2013.01); *Y10T 137/8359* (2015.04)

(58) Field of Classification Search
CPC ... G01N 33/5005; C12M 41/36; C12M 23/22; C12M 23/16; C12M 1/34; C12M 1/3446; C12M 1/3453; C12M 1/3461; C12M 1/3469; C12M 1/3476; C12M 23/34; C12M 23/42; C12M 23/46; C12M 25/00; C12M 25/02; C12M 25/04; C12M 25/14
See application file for complete search history.

(56) References Cited

U.S. PATENT DOCUMENTS

| | | | |
|---|---|---|---|
| 5,290,684 A * | 3/1994 | Kelly | A61F 2/022 435/29 |
| 6,586,235 B1 * | 7/2003 | Banes | C12M 23/10 435/293.1 |
| 7,018,830 B2 | 3/2006 | Wilding | |
| 7,871,824 B2 | 1/2011 | Morozov | |
| 2003/0082632 A1 | 5/2003 | Shumate | |
| 2011/0045993 A1 | 2/2011 | Kent | |
| 2011/0124130 A1 | 5/2011 | Wagner | |

FOREIGN PATENT DOCUMENTS

WO    WO 87-01804 A1    3/1987

\* cited by examiner

*Primary Examiner* — Renee Claytor
*Assistant Examiner* — Susan E Fernandez
(74) *Attorney, Agent, or Firm* — Thomas Horstemeyer, LLP

(57) ABSTRACT

In accordance with the purpose(s) of the present disclosure, as embodied and broadly described herein, embodiments of the present disclosure, in one aspect, relate to a device (or "flow chamber"), methods of making a device, methods of using a device, and the like.

20 Claims, 18 Drawing Sheets

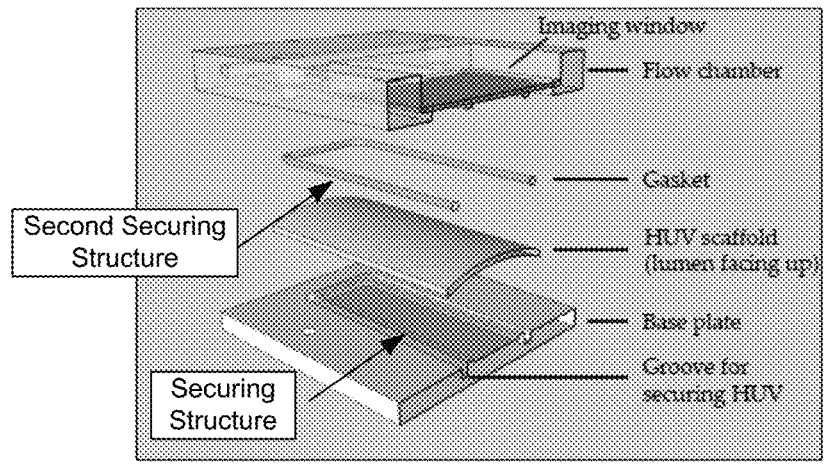
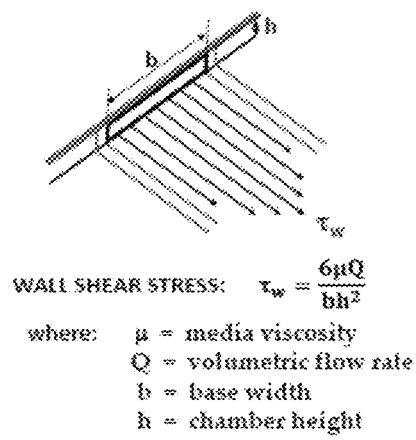
FIG. 2
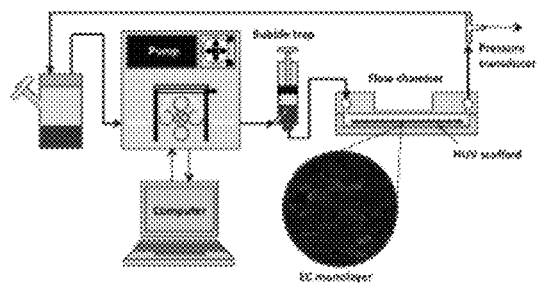
FIG. 3

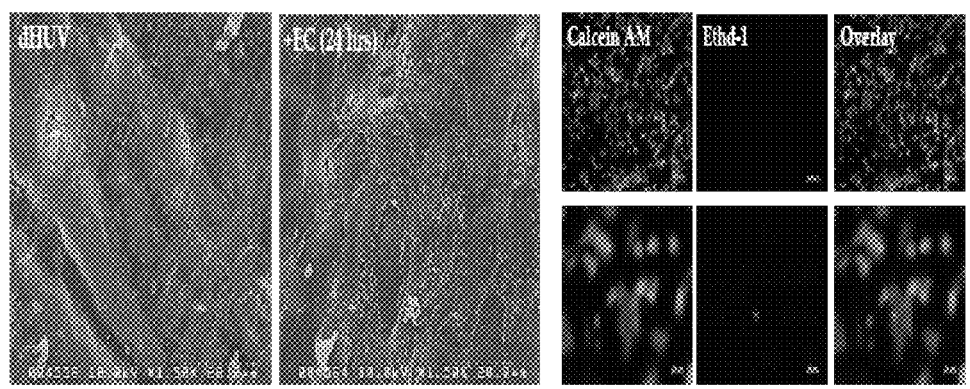
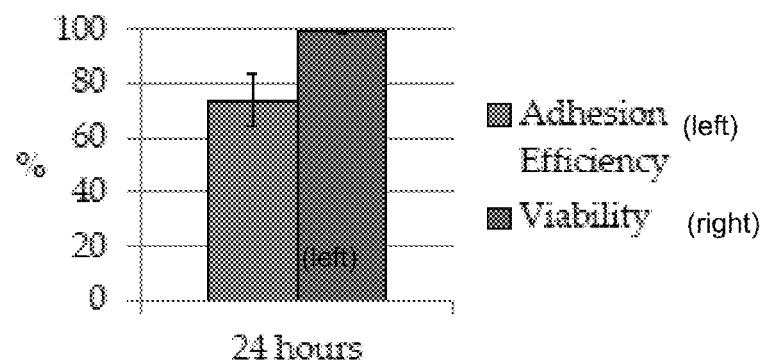
FIG. 4

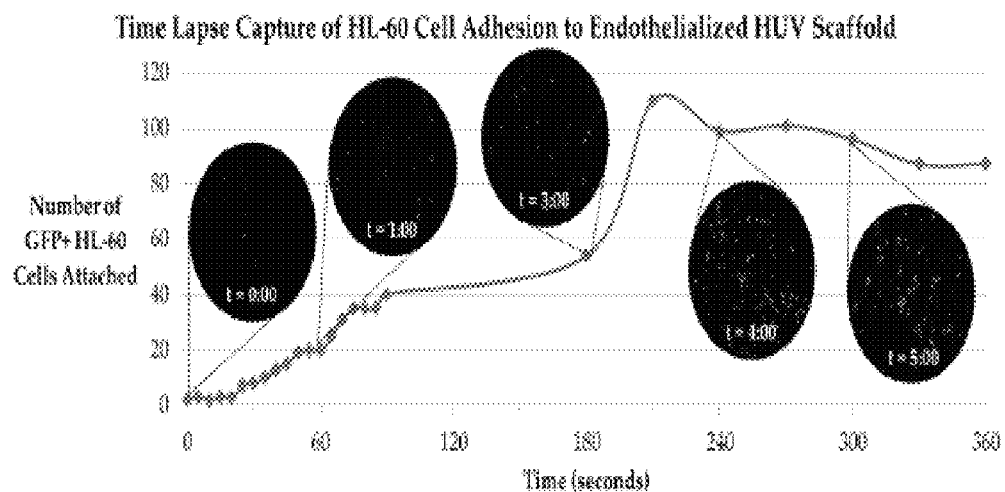
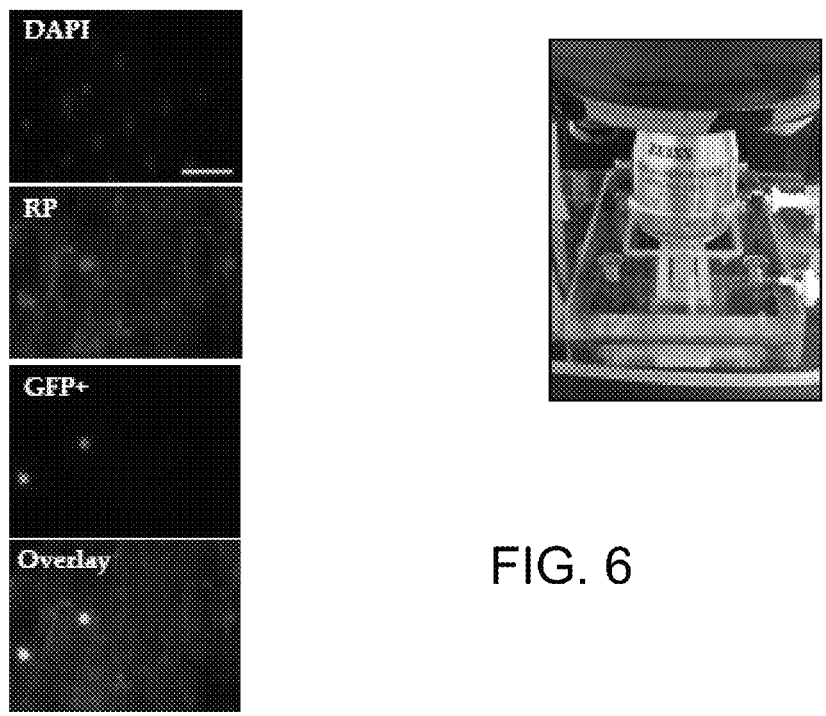
FIG. 6

FLOW CHAMBERS, METHODS OF USING THE FLOW CHAMBER, AND METHODS OF MAKING THE FLOW CHAMBER

CLAIM OF PRIORITY TO RELATED APPLICATION

This application is the 35 U.S.C. §371 national stage application of PCT Application No. PCT/US2012/068387, filed Dec. 7, 2012, which claims priority to U.S. provisional application entitled, "FLOW CHAMBERS, METHODS OF USING THE FLOW CHAMBER, AND METHODS OF MAKING THE FLOW CHAMBER" having Ser. No. 61/568,740, filed on Dec. 9, 2011, which is entirely incorporated herein by reference.

FEDERAL SPONSORSHIP

This invention was made with Government support under Contract/Grant No R01 HL088207, awarded by the National Institutes of Health. The Government has certain rights in this invention.

BACKGROUND

Cell adhesion to the lumenal surface of blood vessels is a dynamic process mediated by the mechanical forces associated with blood flow. Due to the difficulties associated with i) accurately measuring variable hemodynamic forces across different vascular geometries and ii) imaging peripheral cell adhesion events in vivo, parallel plate flow chambers have been used to simulate these processes in a more controllable in vitro setting. These devices produce a parabolic flow velocity profile between two planar surfaces, subjecting each surface to uniform fluid shear stress. However, current devices suffer from deficiencies.

SUMMARY

In accordance with the purpose(s) of the present disclosure, as embodied and broadly described herein, embodiments of the present disclosure, in one aspect, relate to a device (or "flow chamber"), methods of making a device, methods of using a device, and the like.

In an embodiment, a device, among others, includes: a first inlet port at a first end of the device that is configured to flow a first fluid; a flow channel that is in fluidic communication with the first inlet port, wherein the flow channel is configured to hold a sample so the first fluid contacts a side of the sample, an optically transparent viewing window disposed adjacent the flow channel to view the sample in real time as the sample is exposed to the first fluid; and an exit port that is in fluidic communication with the flow channel, wherein the flow channel is configured so that the first fluid flows from the first inlet port side to the exit port side of the flow channel.

In an embodiment, a method of observing cell dynamics in real time, among others, includes: flowing a first fluid in a flow channel, wherein the fluid flows across a scaffold material that includes a plurality of cells; observing the scaffold material and cells through an optically transparent viewing window disposed adjacent the flow channel to view the sample in real time as the sample is exposed to the first fluid; and flowing the first fluid out of the flow channel through an exit port.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 illustrates an embodiment of the membrane flow chamber assembly (cross-sectional view). To create a planar flow channel of uniform height, decellularized human umbilical vein (HUV) scaffold is sliced open axially and spread out over the base plate. A gasket is then used to stretch the HUV membrane in an outer groove around the walls of the base plate channel to secure the scaffold in a tensed conformation. When the plates are screwed together, the HUV is compressed between the top and bottom ridges, creating a tightly sealed channel. This flow chamber can be placed under an upright fluorescence microscope and imaged through the viewing window. The constant cross-sectional area allows the wall shear stress (tw) to be easily predicted according to the Hagen-Poiseuille equation.

FIG. 3 illustrates an endothelial cell perfusion culture system. The membrane flow chamber is used to impose shear stress on endothelial cell (EC) monolayers seeded on decellularized human umbilical vein (HUV) scaffolds in vitro. HUVEC suspensions are injected into the flow chamber and allowed to mature over 48 hours. Peristaltic pumps are used to impose pulsatile flow of culture media over the EC monolayers. The rotational speed of the pumps is controlled by an external computer.

FIG. 4 illustrates an endothelial cell viability on decellularized human umbilical vein. Top left: Human umbilical veins (HUV) were decellularized using 1% sodium dodecyl sulfate, cut open, and affixed to flow chambers. EC seeded on the HUV basement membrane within the flow chamber were assessed for adhesion efficiency and viability after 24 hours. Calcein AM reveals live cells, while ethidium (Ethd-1) stains the nuclei of dead cells. EC attached with 73.7±9.9% efficiency, based on initial seeding concentration. Attached cells showed excellent viability on the basement membrane surface, calculated to be 99.1±0.3% overall (n=5).

FIG. 6 illustrates a time lapse capture of HL-60 cell rolling on endothelialized HUV. Decellularized HUV were seeded with EC monolayers within membrane flow chambers. After flow pre-conditioning, monolayers were activated with 1 U TNF-a for four hours. GFP-transfected HL-60 cell suspensions were perfused across endothelialized HUV scaffolds at a shear stress of 1 dyne/cm$^2$. Images of HL-60 rolling and arrest were captured using a high-resolution monochrome camera on an upright fluorescence microscope. After 6 minutes of perfusion, scaffolds were fixed and stained as previously described. Scale bar: 50 mm.

DETAILED DESCRIPTION

Figure 1:
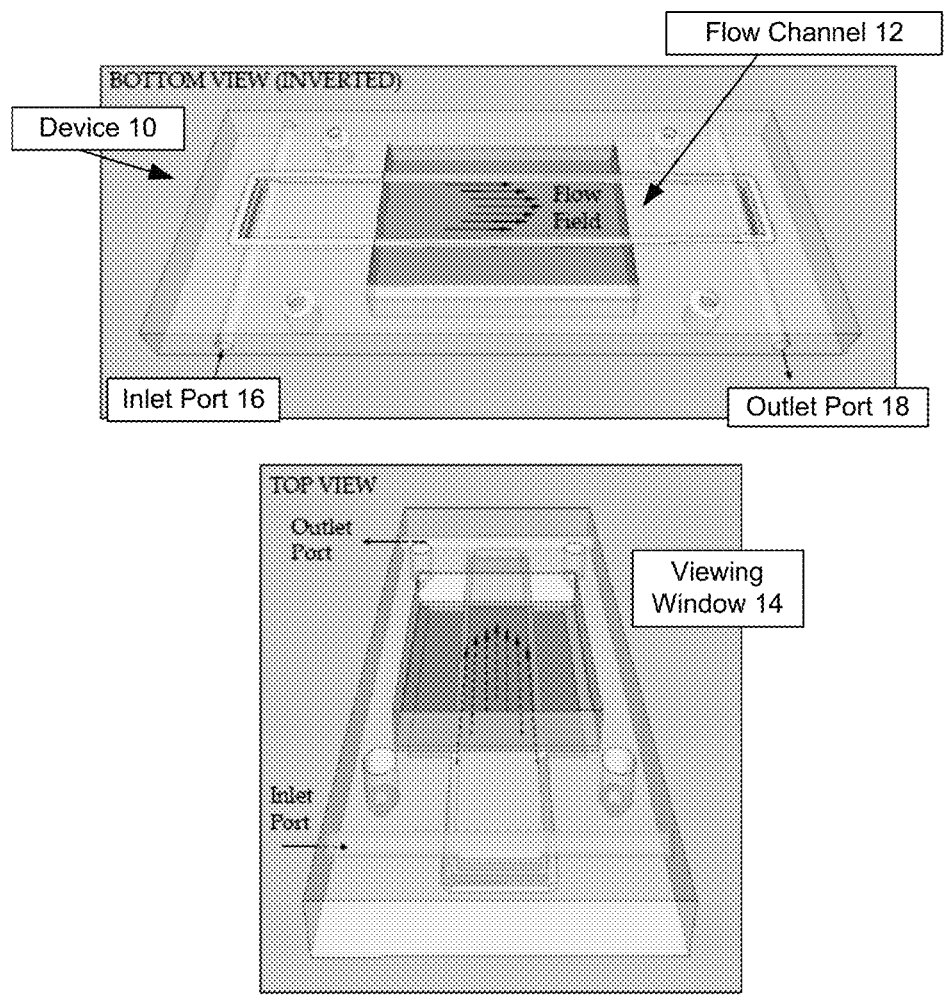
FIG. 1 illustrates an embodiment of the membrane flow chamber. The device was designed to mirror the planar geometry of the commonly used parallel plate flow chamber, producing a channel with uniform fluid mechanics across an endothelial monolayer, while holding a flexible substrate (not shown here). The center portion of the chamber includes a viewing window (highlighted in dark gray) for high-magnification fluorescence microscopy.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Discussion

Exemplary embodiments of the present disclosure provide for a device (or "flow chamber"), methods of making a device, methods of using a device, and the like. Embodiments of the present disclosure can be used to view cell rolling and adhesion on biological or synthetic membranes such as platelets in real time. In addition, the device can be used for screening drugs or other molecules or cells to monitor and observe, in real time, the interactions with the cells on or with a support material (e.g., scaffold material).

In an exemplary embodiment, the device 10 includes a flow channel 12, an optically transparent viewing window 14, a first inlet port 16, and an exit port 18. In an embodiment, the device can be made of a plastic, composite, and/or metal material. The device 10 can be monolithic or made from multiple sections.

In an embodiment, the first inlet port 16 is positioned at or near a first end of the device 10. The first inlet port 16 is in fluidic communication with the flow channel 12 so that a fluid flows through the first inlet port 16 and through an area defined by the flow channel 12. The fluid flows through the flow channel 12 and exits the device 10 via an exit port 18 that is in fluidic communication with the flow channel 12. In an embodiment, the area defined by the flow channel 12 can have a length about 5 mm to 250 mm, a width of about 1 mm to 50 mm, and a height of 25 μm to 10 mm.

In an embodiment, two or more inlet ports can be used to flow two or more types of fluids (e.g., different components present in each fluid). In an embodiment, two or more exit ports can be included in the device. The inlet and exit ports can be controlled manually and/or with a control device to regulate the flow of one or types of fluids into the flow channel 12.

In an embodiment, the fluid can include whole blood or other media solutions that support or maintain cell populations, for example phosphate buffered saline or other cell culture media. In an embodiment, the fluid can include a drug and the sample can be observed as the drug interacts with the sample as a function of time, flow rate, concentration of drug and/or other components, and the like.

In an embodiment, the device 10 includes an optically transparent viewing window 14 disposed adjacent the flow channel 12 to view the sample in real time as the sample is exposed to the fluid. The term "adjacent" can mean touching or separated by a short distance from something else. In an embodiment, the viewing window 14 can be made of a material so that the sample and cells can be observed. In an embodiment, the viewing window 14 can be made of plastic, glass, or the like. In an embodiment, the viewing window 14 can have the same or nearly the same length and width as the flow channel 12. In an embodiment, the viewing window 14 covers only a portion of the flow channel 12. Where the viewing window 14 covers the flow channel 12, the viewing window 14 is a side of the flow channel 12 that defines the area where the sample and fluid are disposed, where other portions of the device 10 define the remaining portions of the flow channel 12. In an embodiment, the viewing window 14 can have a thickness in the µm to 10s of cm range. In an embodiment, the flow channel 12 includes a sample, such as a scaffold material. In an embodiment, the scaffold material can be made of a synthetic material (e.g., Dacron, Cortex), a biological material (e.g., a tissue), or a combination thereof. In an embodiment, the scaffold material includes a plurality of cells (e.g., stem cells, endothelial cells, smooth muscle cells, leukocytes, platelets or other circulating cells either progenitor or primary as well as leukemic cells or other cancer cell lineage) on the and/or within the scaffold material. The sample can be positioned appropriately along the dimensions (length, width, or height) of the flow channel 12. In an embodiment, the sample is positioned so that the sample can be observed through the viewing window 14. In an embodiment, the distance from the viewing window 14 to the sample can be kept at a minimum so that cells, for example, can be observed. In an embodiment, the distance from the sample to the viewing window 14 can be about 25 µm to 10 mm. In an embodiment, the fluid can be flowed across the top and/or bottom of the sample. In an embodiment, one fluid can be flowed across the top of the sample and another fluid can be flowed across the bottom of the sample.

In an embodiment, the flow channel 12 includes a securing structure for securing the sample to the flow channel 12. In an embodiment, the securing structure includes a groove that secures the sample to the flow channel 12. In an embodiment the groove can extend the length and width of the flow channel 12 or can be extend across the width only or the length only. In an embodiment, the sample can be secured in the groove using one or more securing mechanisms. In an embodiment the flow channel 12 includes a second securing structure (e.g., a gasket or O-ring), where the sample is disposed between the groove and the second securing structure.

In an embodiment the flow channel 12 includes a ridge (e.g., along the edge of the groove) or other similar structure so that the sample is not disposed against the bottom of the flow channel 12. In an embodiment, a second inlet port can flow a fluid across the bottom of the sample. In an embodiment, a second viewing window can be positioned along the flow channel on the opposite side of the viewing window to view the sample from the other side as it interacts with the fluid.

In a particular embodiment as described in the Examples, the device can include a flow chamber having an optically transparent section to view from the top down onto the material in the flow chamber. In an embodiment, the cut away section has a glass or plastic coverslip built into the polycarbonate block and is recessed into the block such that the lower surface is continuous with the top of the flow field. This allows the use of opaque material to be viewed at high magnification and to monitor, in real time, adhesion or surface changes. In an embodiment, the lower plate has a channel and ridge design that seals the compartment and is machined to a specific height to cater to a specific material, whilst controlling the height value. In an embodiment, the lower plate may optionally have a secondary flow field under the primary flow field (opposite side of the material being assessed). This can be used to control or modulate: multiple flow fields, diffusion gradients, pressure gradients, combinations thereof, as part of the pump system or continuous perfusion system. Additional details regarding embodiments of the present disclosure are provided in the Examples.

In an embodiment, the cell dynamics (e.g., adhesion, infiltration) can be observed in real time using embodiments of the device. In an embodiment, the cells can be positioned on or within a scaffold structure. Then a fluid is flowed across in a flow channel and interacts with the scaffold structure and then exits the exit port. In real time the scaffold material can be observed through the optically transparent viewing window that is positioned adjacent the flow channel. In an embodiment, an imaging device (e.g., microscope, digital camera, or the like) can be positioned adjacent the viewing window, where the term adjacent can be close to or touching. In an embodiment, the microscope can be about 25 µm to 10 mm, from the scaffold material.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Introduction:
Endothelialization of vascular grafts has been used as a tissue engineering strategy to minimize platelet adhesion, leukocyte infiltration, and other unfavorable host responses that lead to graft failure. Assessment of vascular grafts' intimal reactivity is commonly performed by flowing whole blood across the lumenal (blood-contacting) surface. However, performing such experiments at physiological shear rates requires high volumes of whole blood, and only end-point assessment is possible due to the closed vascular geometry. Here we describe the development of a new flow chamber designed for 1) seeding and conditioning of an endothelium under defined shear conditions on a decellularized vascular surface and 2) live imaging of interactions between the opaque scaffold and fluorescently labeled blood cells.

Flow Chamber Design:

OBJECTIVE: To develop a novel flow chamber for the seeding and culture of endothelial cells on biologically relevant surfaces under defined shear stress conditions.

Design Criteria:

1. The flow chamber must permit live imaging of platelet and/or leukocyte adhesion onto the membrane surface at high-magnification (40×). A viewing window was incorporated into the flow chamber in order to permit live imaging. The focal distance between the substrate surface and the top of the flow chamber was shortened enough to allow observation of EC, leukocytes, and platelets at 40× magnification (long working distance objective).

2. The design must accommodate biological membranes of varying thickness. Due to variations in scaffold thickness, especially using ex vivo-derived tissues, the device is by design capable of holding tissues at a range of thicknesses (0.5-1.5 mm).

3. The chamber volume must be minimal (less than 1 mL). In addition to reducing the media requirements during perfusion culture, the low chamber volume (400 mL) will conserve reagents used in fluorescent staining of endothelial monolayers in situ (e.g., viability assays) or blood flow experiments (e.g., tagged leukocytes or platelets).

Materials and Methods:

An acrylic (e.g., other materials can be used to make the chamber) flow chamber was designed and built to facilitate perfusion across a flexible (opaque) biological scaffold using a parallel plate flow channel. The device was designed to allow direct imaging of fluorescently tagged platelets and/or leukocytes as they attach to the basement membrane in real time at high magnification. The device was tested for its capacity to seed and maintain endothelial viability under perfusion conditions for an extended culture period. Time lapse fluorescence imaging was conducted to capture adhesion of GFP-expressing HL-60 cells to activated endothelia in real time.

Figure 5:
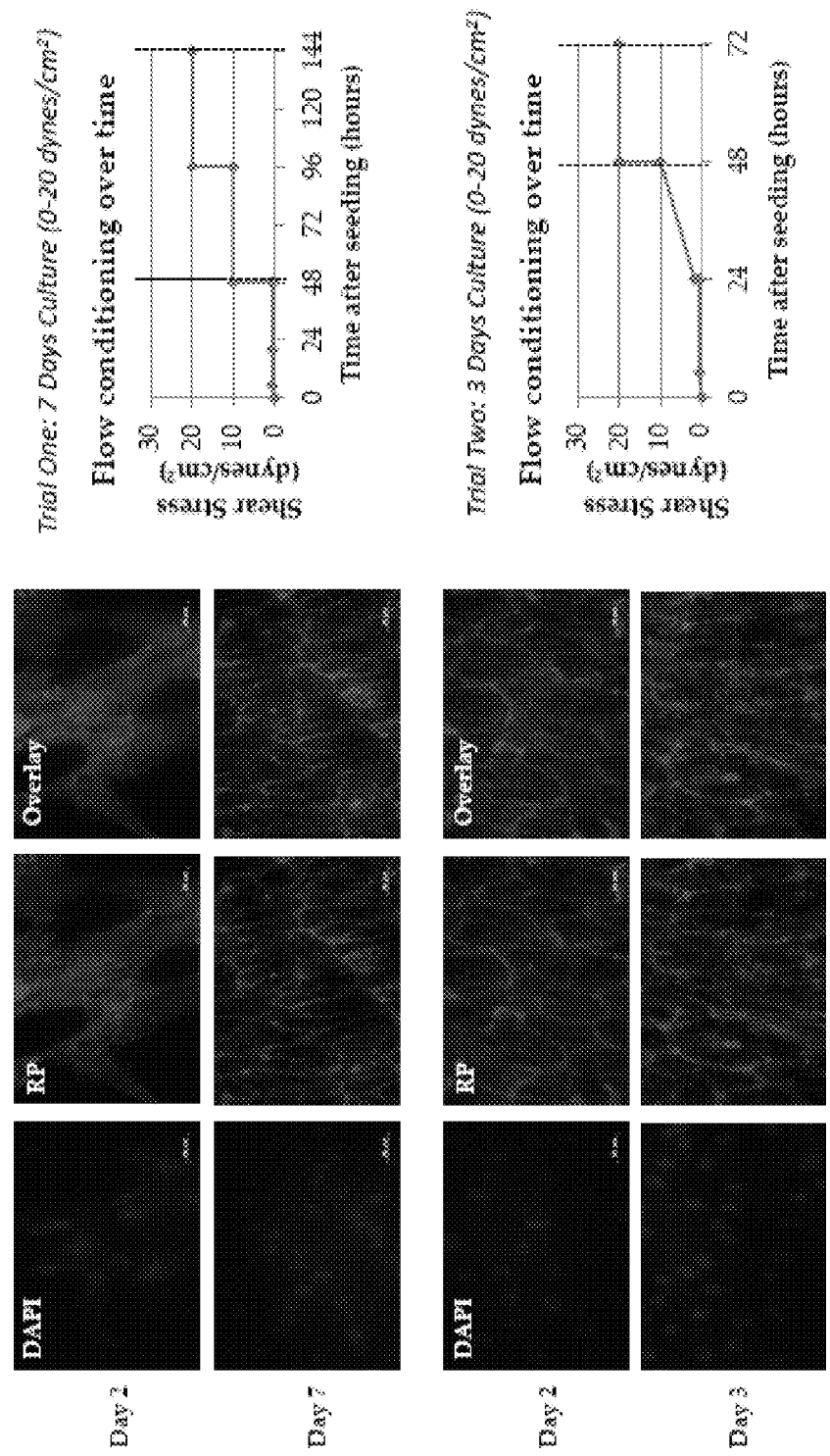
FIG. 5 illustrates a cytoskeletal morphology of flow-conditioned EC on HUV surface (above). Decellularized HUV were seeded with EC monolayers within membrane flow chambers, flow-conditioned, and fixed and co-stained with rhodamine phalloidin and DAPI to visualized f-actin and nuclei, respectively. Trial one (top): Results show that EC developed confluent monolayers that could survive one week of perfusion culture. Trial two (bottom): Flow conditions were empirically optimized (using a ramped flow regime programmed into the pumps) to produce a confluent cell monolayer 48 hours after initial seeding that could withstand physiological levels of shear stress (20 dynes/cm$^2$). Scale bar: 25 mm.

Results:

The flow chamber assembly is shown in FIGS. 1, 2, and 3. The decellularized human umbilical vein is sliced open axially and compressed between two acrylic plates, creating a flow channel of uniform height. Primary human umbilical vein endothelial cells (HUVEC) were seeded and maintained under perfusion for 7 days (FIG. 5). A live-dead assay revealed high endothelial cell viability (>99%) on the lumenal HUV surface (FIG. 4). DAPI/rhodamine phalloidin co-staining revealed a confluent endothelial monolayer with uniform cytoskeletal alignment in the flow direction (FIG. 2). HL-60 cell rolling adhesion to endothelialized HUV was captured in real time using time lapse imaging (FIG. 6). These results demonstrate that the device can be used effectively for comprehensive assessment of engineered vascular surfaces.

Discussion

Details of the microenvironment in which endothelial cells reside are critical to their behavior. Not only does the physical composition of the basement membrane contribute via integrin signaling, but the mechanical properties (e.g., stiffness, topography, etc.) of the substrate can influence their transduction of hemodynamic shear stress. Thus, culture of endothelial cells on a decellularized vascular surface may be more appropriate for studies in mechanotransduction. The chamber not only provides an environment more reminiscent of the vascular intima, but also permits live visualization of endothelial cells cultured under flow, and is also useful for studies in leukocyte rolling and platelet adhesion and aggregation. This chamber has been successfully tested with the human umbilical vein and human amniotic membrane, and can be adapted for a wide range of other conduit biomaterials.

Example 2

Brief Introduction:

Adhesion of circulating blood cells to the vascular wall is involved in numerous wound healing processes and clinical pathologies that are yet to be fully understood. Parallel plate flow chambers have been used to simulate these dynamic processes in vitro, where fluid mechanics can be controlled and imaging can be conducted in real-time. Cell adhesion at the surface of implantable vascular grafts, however, can only be assessed terminally after perfusion due to opacity of these materials. Here we describe the design of an innovative flow chamber for real-time analysis of blood-biomaterial interactions under flow. Decellularized human umbilical vein (HUV) was used as a vascular model to temporally observe and characterize platelet, leukocyte, and endothelial cell adhesion dynamics on a natural basement membrane (BM). Viable, confluent endothelial cell monolayers were seeded on the BM, conditioned to resist arterial shear stress levels (up to 24 dynes/cm$^2$) over a 48 hour period, and maintained under perfusion for up to one week. The BM was imaged while whole blood/neutrophil suspensions were perfused across the HUV surface to quantify cell accumulation. This novel design facilitates live visualization of dynamic events including cell adhesion, migration, and morphological adaptation at the blood-graft interface, and can be used for preliminary assessment of clinically relevant biomaterials before implantation.

Introduction:

Cell adhesion to the lumenal surface of blood vessels is a dynamic process mediated by the mechanical forces associated with blood flow. Due to the difficulties associated with i) accurately measuring variable hemodynamic forces across different vascular geometries and ii) imaging peripheral cell adhesion events in vivo, parallel plate flow chambers have been used to simulate these processes in a more controllable in vitro setting. These devices produce a parabolic flow velocity profile between two planar surfaces, subjecting each surface to uniform fluid shear stress. (Frangos, Eskin et al. 1985; Bacabac, Smit et al. 2005; Reinhart-King, Fujiwara et al. 2008) Glass, polystyrene, or other optically transparent substrates can then be coated with cells or proteins, or micropatterned with selectively adhesive peptides/non-adhesive monomers to observe cell adhesion under flow using conventional light microscopy. Much of our current understanding of the role shear plays in cell signaling, protein conformational changes, and other phenomena associated with peripheral cell adhesion has been obtained through the use of parallel plate chambers. (Frangos, Eskin et al. 1985; Frangos, McIntire et al. 1988; Schmidtke and Diamond 2000) Cell adhesion is also a critical consideration with implantable biomedical devices, particularly in vascular grafts where surface properties are critical to graft success.

Thrombus formation, characterized by excessive platelet adhesion and aggregation, is a significant cause of occlusive failure of vascular grafts (Mehta, Izzat et al. 1997; Kannan, Salacinski et al. 2005). As such, persistent efforts have been made to produce materials resistant to protein adsorption and peripheral cell attachment. (de Mel, Jell et al. 2008; Kapadia, Popowich et al. 2008) As part of the design process, an important precursor to clinical implantation is a global assessment of the biomaterial's inherent reactivity with blood. (Sarkar, Sales et al. 2007) Currently, preclinical characterization of a material's resistance to cellular adhesion and infiltration has been typically assessed in vivo using vascular bypass (L'Heureux, Dusserre et al. 2006) or ex vivo shunt models (Yazdani, Tillman et al. 2010). A significant drawback associated with the use of animal models is that the assessment can only be performed terminally. While useful for predicting long-term patency of implanted biomaterials, animal trials are expensive and time consuming, and more conservative strategies that offer a higher throughput while being cost effective have been sought.

Given the practical advantages of real-time, non-invasive imaging of these events, we sought to develop a device that could be used to monitor cell adhesion on the opaque surfaces of clinically implantable vascular biomaterials. Here we detail the design of a novel parallel plate flow chamber for real-time observation of peripheral cell adhesion and morphological adaptation on a model vascular biomaterial under controlled shear stresses. Using labeled whole blood and select cell suspensions, we demonstrate the capability of this device to permit live capture of dynamic cell adhesion events at the intimal surface of naturally-derived blood vessels using time lapse fluorescence microscopy. We also validate the use of this flow chamber for long-term culture of neo-endothelia and optimize a flow pre-conditioning regime that yields confluent endothelial cell monolayers resistant to arterial shear stresses. These assays demonstrate the versatility of this device for improved in vitro modeling of physiological cell adhesion events as they occur in vivo.

Materials and Methods

Cell Culture:

Human umbilical vein endothelial cells (HUVEC) were sourced from umbilical cords obtained from the Labor & Delivery unit at Shands Hospital at the University of Florida (Gainesville, Fla.) and processed within 12 hours of birth. Endothelial cells (EC) were isolated from cords using collagenase perfusion, as previously described by Jaffe et al. (Jaffe, Nachman et al. 1973) Cells were maintained in VascuLife basal medium supplemented with VEGF LifeFactors kit (LifeLine Cell Technologies; Frederick, Md.) and 100 U/mL penicillin/streptomycin (HyClone; Logan, Utah) at 37° C. with 5% $CO_2$, and used experimentally between P2 and P5.

HL-60 promyelocytic leukemia cells transduced with a green fluorescent protein (GFP)-expressing lentiviral vector were generously provided by Dr. Christopher Cogle (University of Florida Department of Medicine, Gainesville, Fla.). They were maintained at $5 \times 10^5$-$2 \times 10^6$ cells/mL in Dulbecco's Modified Eagle Medium (Hyclone) supplemented with 20% FBS.

Blood Draws:

Human venous blood was harvested from healthy adult volunteers after obtaining informed consent (IRB approval #689-2010). Blood was collected in 10 U of heparin using a 21-gauge needle. Platelets were fluorescently labeled with 20 pg/mL of Acridine Orange (Molecular Probes; Grand Island, N.Y.) and used immediately in perfusion experiments.

Dissection and Decellularization of Human Umbilical Veins:

Human umbilical veins (HUV) were isolated from the surrounding tissue using an automated dissection procedure that has been described previously. (Daniel, Abe et al. 2005) In brief, umbilical cords were rinsed clean and cut into 10 cm sections. A stainless steel mandrel (¼" OD) was inserted through the vein and then progressively frozen down to −80° C. After at least 24 hours, frozen cords were machined to a uniform wall thickness of 750 microns using a CNC lathe (MicroKinetics, GA, USA). Veins were progressively thawed at −20° C. for 2 hours then at 4° C. for 2 hours. Veins were then decellularized by immersion in 1% (w/v) solution of sodium dodecyl sulfate (SDS) in DI water under orbital shaking (100 RPM) for 24 hours at a 1:20 mass to volume ratio, then rinsed in DI water under orbital shaking for 5 minutes, 15 minutes, 40 minutes, 1 hour, 3 hours, 12 hours, and 24 hours. HUV sections were then incubated in 70 U/mL of deoxyribonuclease I (Sigma-Aldrich; St. Louis, Mo.) in PBS agitated on an orbital shaker for 2 hours at 37° C. Sections were rinsed in DI water (2×) for 5 minutes and terminally sterilized in a solution of 0.2% peracetic acid and 4% ethanol in DI water on an orbital shaker for 2 hours. Scaffolds were rinsed for 5 minutes, 15 minutes, 40 minutes, and 1 hour in DI water, and pH balanced in PBS (pH 7.40) for 24 hours. Scaffolds were stored in PBS at 4° C. for a maximum of 2 weeks until use.

Platelet Adhesion (Acellular Scaffolds):

With the HUV mounted into the flow chamber whole blood was perfused across the HUV surface at a wall shear stress of 2 dynes/cm², calculated according to the Hagen-Poiseuille equation:

$$\tau = \frac{6\mu Q}{bh^2} \quad (1)$$

where m is viscosity, Q is mean volumetric flow rate, and b and h are the base width and channel height, respectively. A longpass emission filter (>530 nm) was used to detect fluorescently labeled platelets using RNA binding acridine orange (Molecular Probes; 460/650 nm). Platelets were perfused continuously over a 5 minute period, with images were captured every 15 sec for dynamic observation of aggregate formation. At one minute intervals, a threshold was applied to obtain a representative black and white mask of each image with the percentage of white area corresponding to the percentage of platelet coverage.

Light intensity profiles of nine aggregates were plotted and thresholded at a gray value of 80 (light intensity of a platelet). Length of aggregates was normalized by dividing data above threshold in 20 portions and averaging each portion. All nine normalized profiles were then averaged giving a global platelet aggregate light intensity profile.

Perfusion Culture System:

Assembled flow chambers were connected to a media reservoir fitted with a 0.22 mm filter for gas exchange. The entire system was placed in a dehumidified incubator maintained at 37° C. and 5% $CO_2$. The flow rate through the chamber was directly modulated by the rotational speed of the peristaltic pump, which was controlled by Masterflex Linkable Instrument Control Software V3.1. The mean wall shear stress to which EC were exposed was calculated according to equation 1 (assuming steady flow) as described above.

Endothelial Cell Seeding:

Assembled flow circuits were sterilized with a solution of 4% ethanol, 0.2% peracetic acid and balanced with phosphate-buffered saline (pH 7.4). Standard endothelial cell media (2% FBS) was flowed through the system prior to seeding. Endothelial cell suspensions ($10^6$ cells/mL) were inoculated into the flow field and allowed to settle, attach, and spread out on the scaffold surface for 5 hours before initiating flow.

Endothelial Cell Viability Assay:

EC monolayers were assessed for viability using the Live/Dead Viability/Cytotoxicity Kit for mammalian cells (Invitrogen; Grand Island, N.Y.) according to kit instructions. Briefly, scaffolds were first rinsed in PBS, and then incubated for 30 minutes with 2 mM calcein AM and 2 mM ethidium homodimer-1. Images were captured as described below through both the GFP and DsRed filters to visualize live and dead cells, respectively.

Endothelial Cell Staining:

At the end of each experiment, scaffolds were rinsed in PBS, formalin-fixed, and co-stained using rhodamine Phalloidin/4',6-diamidino-2-phenylindole, dihydrochloride (DAPI, 3 nM) (Invitrogen). Imaging was conducted as described below.

Figure 8:
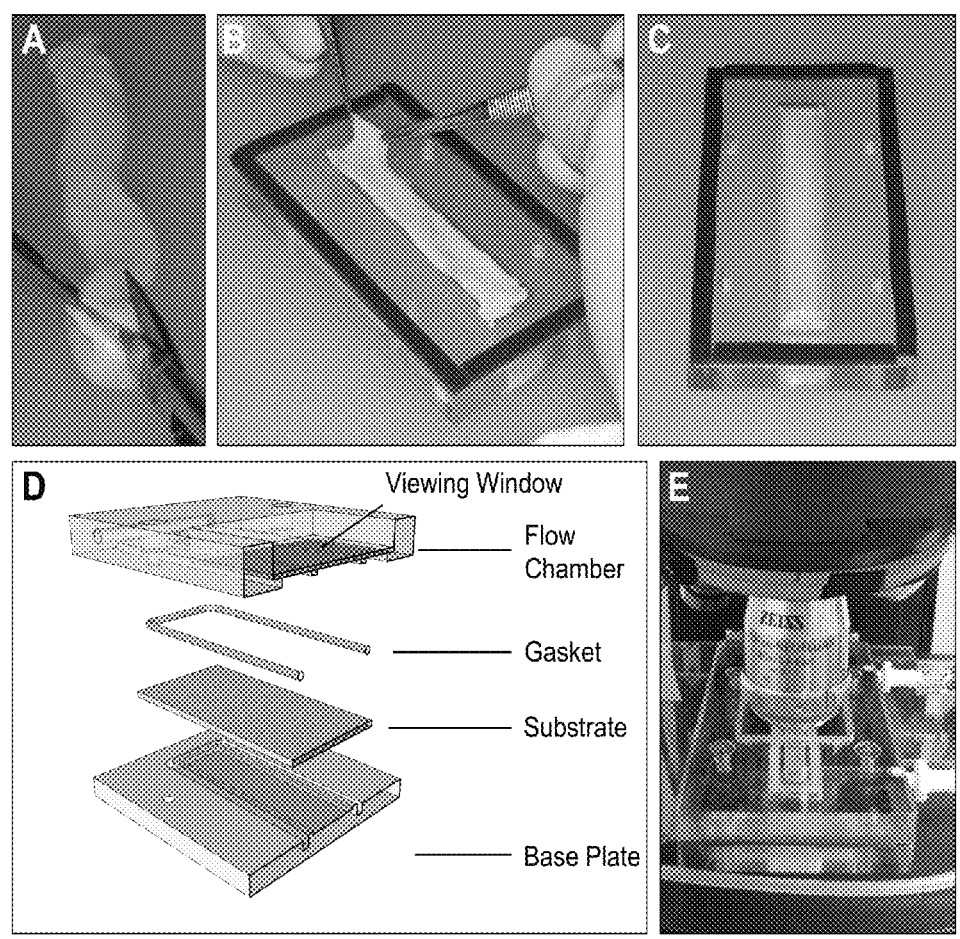
FIGS. 8A-8D illustrate an embodiment of a flow chamber assembly. Decellularized human umbilical vein (HUV) scaffolds were cut open axially (A) and affixed to a base plate (B) using a compressible gasket (C). The base plate was then tightly screwed to the flow chamber, creating a parallel plate flow profile across the HUV surface. A cross-sectional view of the various components is shown in (D). Assembled flow chambers could then be placed on the stage of an upright epifluorescence microscope for high magnification real-time imaging of adhesive interactions between fluorescently labeled cells and the scaffold's surface (E).

Neutrophil adhesion to endothelialized HUV: GFP+HL-60 cells were differentiated into neutrophils by exposure to 1.3% DMSO (Fisher Scientific; Hampton, N.H.) for 3 days, as previously described. (Mollinedo, Lopez-Pérez et al. 2008) Endothelialized HUV scaffolds were activated for four hours by adding 1 U recombinant human TNF-a (Thermo Scientific; Hampton, N.H.) to the media reservoir. Flow chambers were then removed from the incubator and placed on the stage of a Zeiss Axiolmager M2 upright fluorescence microscope (see FIG. 8). Neutrophil suspensions ($10^6$ cells/mL) were then drawn through the flow chamber at a calculated wall shear stress of 1 dyne/cm$^2$ using a programmable syringe pump (Harvard Apparatus). Time lapse imaging of neutrophil adhesion to endothelialized HUV was then performed over a 5 minute period. Culture media without cells was flowed through for an additional minute in order to remove non-adherent cells. Monolayers were fixed using 10% formalin and co-stained as described above.

Scanning Electron Microscopy (SEM):

HUV samples were fixed in 2.5% glutaraldehyde, washed in PBS, fixed in 1% osmium tetroxide solution, and progressively dehydrated in 25%, 50%, 75%. 85%, 95%, and 3×100% ethanol solutions. Samples were then critical point dried, sputter coated with gold/palladium, and imaged using a Hitachi S-4000 FE-SEM (10.0 kV).

Fluorescence Microscopy:

Imaging was conducted using a Zeiss Axiolmager M2 upright fluorescence microscope coupled with an AxioCam HRm Rev. 3 digital camera operated by AxioVision software version 4.8.

Results

Figure 7:
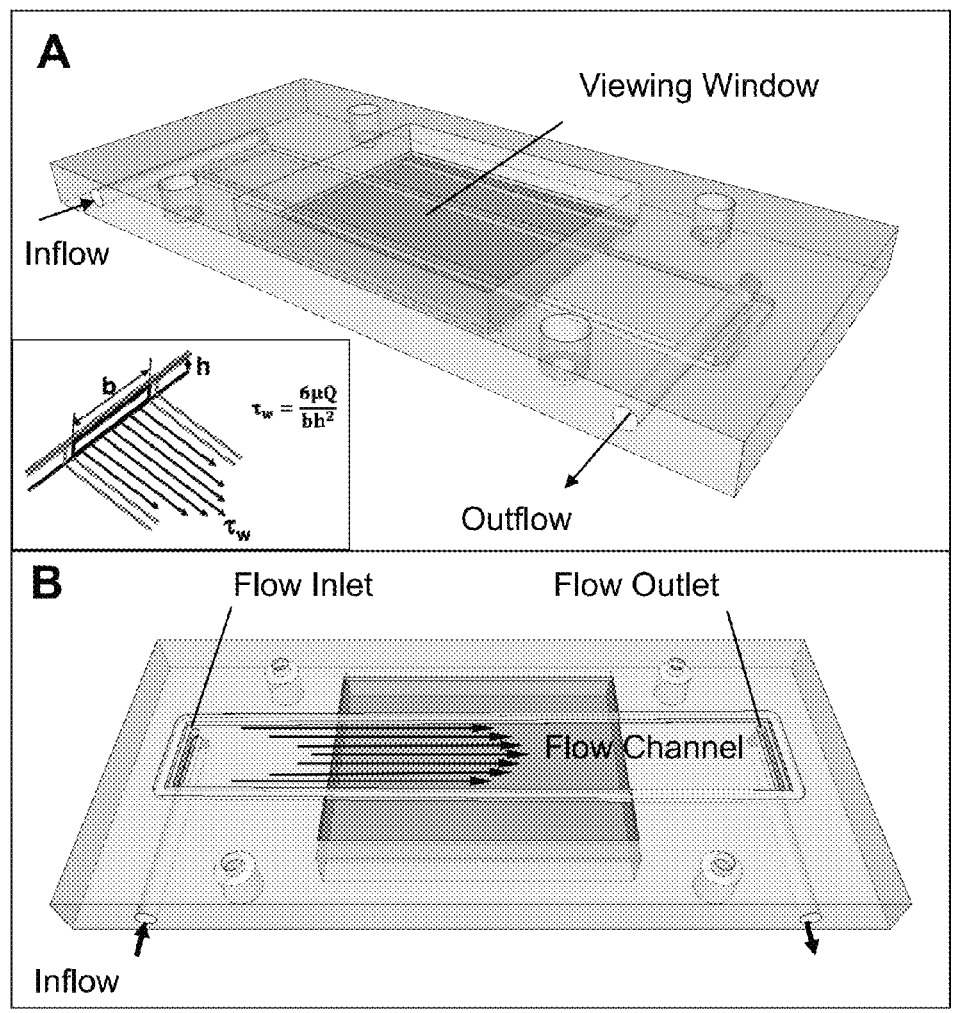
FIGS. 7A and 7B illustrate an embodiment of a flow chamber design. The main body design of the flow chamber is shown in (A). Culture media/cell suspensions are delivered through inflow/outflow ports. An acrylic viewing window was bonded to the center of the flow field to accommodate high-magnification imaging under flow. The flow field is composed of an acrylic chamber and substrate (not shown) in parallel plate geometry, which allows for simple shear stress calculations. The inset schematic shows how wall shear stress ($\tau_w$) at the material's surface is calculated with respect to the flow field dimensions (see equation 1). (B): Inverted view of the flow chamber.

Flow Chamber Design and Assembly:

A parallel plate flow chamber was designed to perfuse fluid (culture media or peripheral blood) across an opaque substrate in an observable environment. Three design criteria were considered paramount: 1) that live imaging can be conducted under high magnification (40× or greater) for dynamic visualization of platelet adhesion, 2) that the device be capable of maintaining parabolic flow while accommodating scaffolds of various thicknesses, and 3) that the reagent volume required to fill the chamber be minimized to conserve blood resources. A significant challenge was decreasing the distance between the top of the chamber and the substrate to allow the focal plane of the microscope objective to reach the scaffold surface. To accomplish this, a thin acrylic slide was bonded over two lanes forming the walls of the flow channel to create a viewing window (see FIGS. 7A and 7B) with a total distance of 1.6 mm. With this design a 40× Zeiss objective (LD Plan-Neofluar) with a maximum working distance of 2.9 mm was compatible for high-magnification imaging of cell adhesion within the flow chamber. Decellularized human umbilical vein (HUV) scaffolds of uniform thickness (750 mm), prepared as previously described (Daniel, Abe et al. 2005), were sliced open axially and affixed to acrylic base plates in a slightly tensed conformation using a compressible silicone gasket (see FIGS. 8A-8C). The main body of the flow chamber was then screwed to the base plate, creating a sealed parallel plate flow channel with the bottom plate composed of the lumenal HUV surface (see FIGS. 8D-8E). By minimizing the base width (b) and height (h) of the flow field (b 6.35×h 0.60 mm), the volume required to fill the flow channel was reduced to <300 mL, approximately 20% of the volume of the native HUV vessel (average diameter 5-6 mm).

Figure 9:
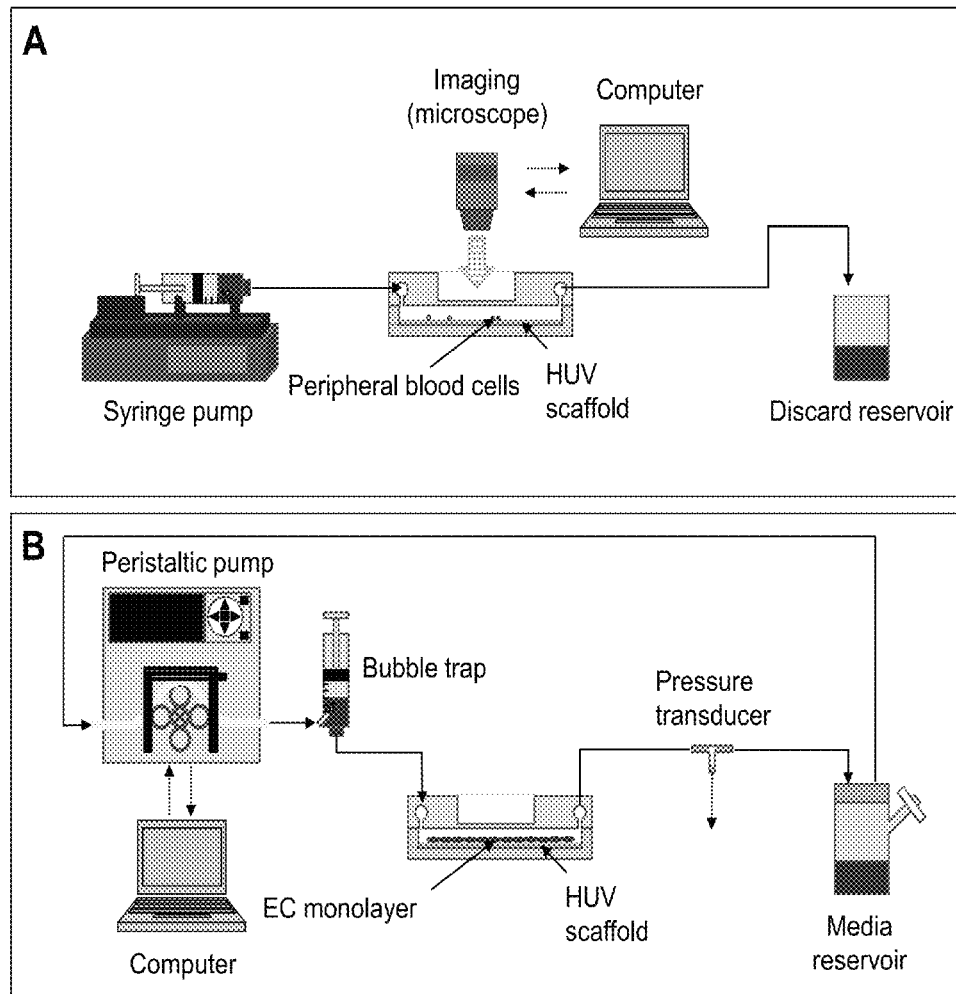
FIGS. 9A-9B illustrate a perfusion system for imaging initial adhesion events or extended culture under flow. A: Short-term imaging schematic. Syringe pumps were used to inject whole blood/cell suspensions through the flow chamber under defined shear conditions. A high-speed camera captured binding events of fluorescently labeled cells at high magnification through a long working distance microscope objective. B: Long-term recirculating perfusion culture. Computer-controlled peristaltic pumps were used to modulate the flow across endothelialized HUV membranes. A bubble trap/pulse dampener was incorporated to abate endothelial cell denudation, while a pressure transducer was used to monitor pressure downstream of the flow chamber.
Figure 10:
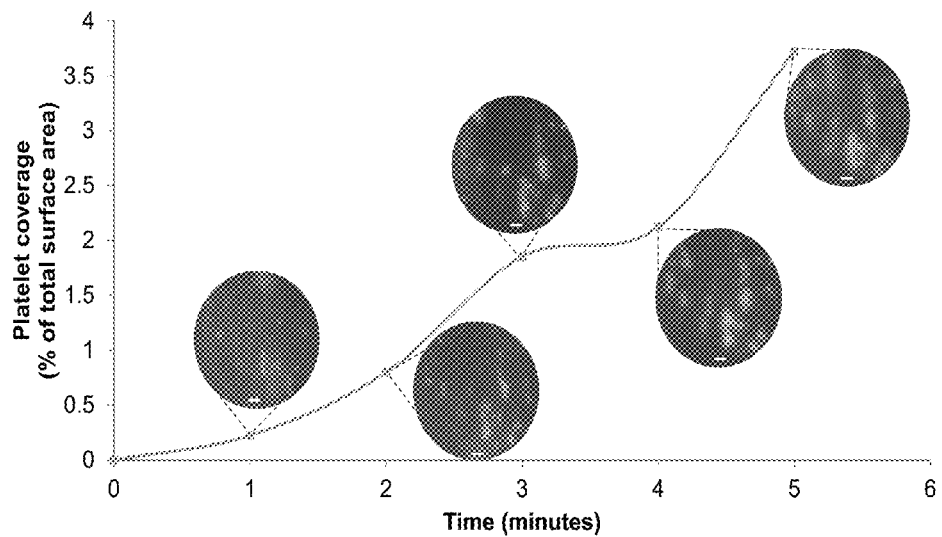
FIG. 10 illustrates a real-time observation of platelet adhesion to acellular human umbilical vein. Whole blood was perfused on the surface of the SDS decellularized HUV at a shear stress of 2 dynes/cm$^2$. Platelet adhesion and aggregation was imaged via epifluorescence microscopy over a five minutes period. Scale bars: 10 μm.

Real-Time Observation of Platelet Adhesion:

As an assessment of platelet adhesion, acridine orange-labelled whole blood was perfused across the acellular HUV and visualized at 40× magnification (see FIG. 9A). Platelets were shown to progressively adhere to the surface forming aggregates that elongated in the direction of flow. Coverage reached 3.7% of the total area over the 5 minute perfusion period (see FIG. 10). Aggregate length ranged from 4.5 µm to 25 µm, depending on the experimental time point from initial adhesion to flow termination, with an average final length of 11.6 µm (±1.2 µm).

Figure 11:
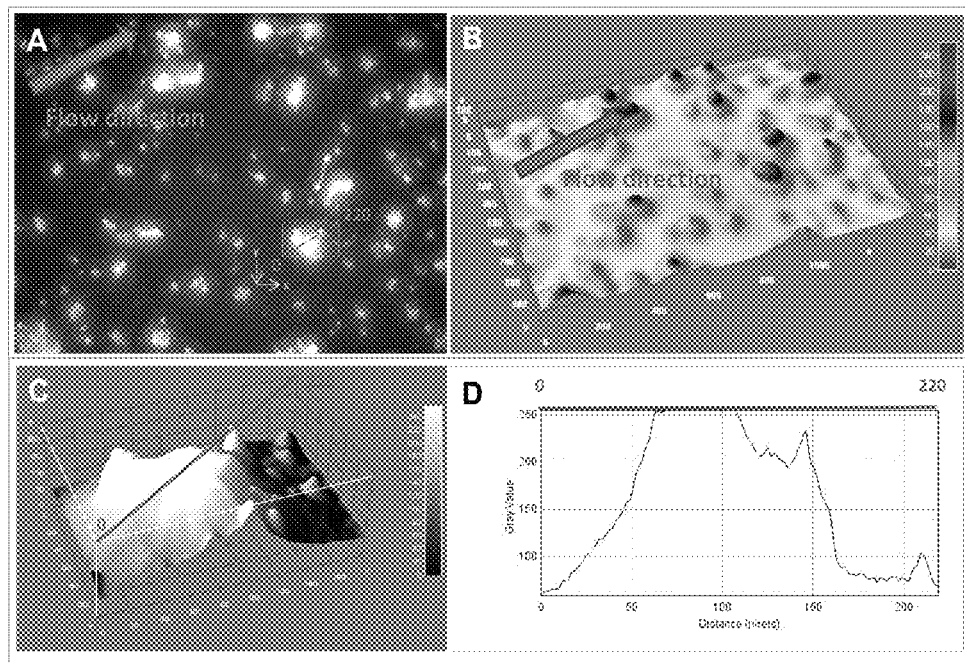
FIGS. 11A-11D illustrate flow induced platelet aggregate geometries. Whole blood was perfused over the surface of SDS decellularized HUV at a shear stress of 2 dynes/cm$^2$. At 10 minutes, 25 z-stack images were taken (2 μm apart). A combined image made of maximum intensity of all z-stacks is presented in panel A, and a 3D light intensity profile of this image in panel B. The platelet aggregate framed in panel A was further analyzed along the 220 pixels long red line; its 3D (C) and 2D (D) light intensity profiles were created.

3D Profiling of Platelet Aggregates:

After 10 minutes of blood flow, numerous platelet aggregates had formed on the HUV basement membrane. Z-stack imaging was conducted to characterize the geometric distribution of platelets within aggregates in z-direction (perpendicular to the surface). 25 sections of 2D images were collected each at 2 µm stepped depths, and a composite image was created by combining the maximal intensity profiles of each z-stack image (see FIG. 11A). Because the maximal intensity of each section corresponds to in-focus platelets, the light intensity of the composite 3D image correlates with the overall shape of the observed aggregate, with white representing the maximum height and black the minimum. Light intensity plots and 3D profiles of platelet aggregates were created using ImageJ plug-in Interactive 3D Surface Plot v2.33 (see FIG. 11B-11D). (Barthel 2011) A plateau was observed when the maximum intensity (white) was reached.

Figure 12:
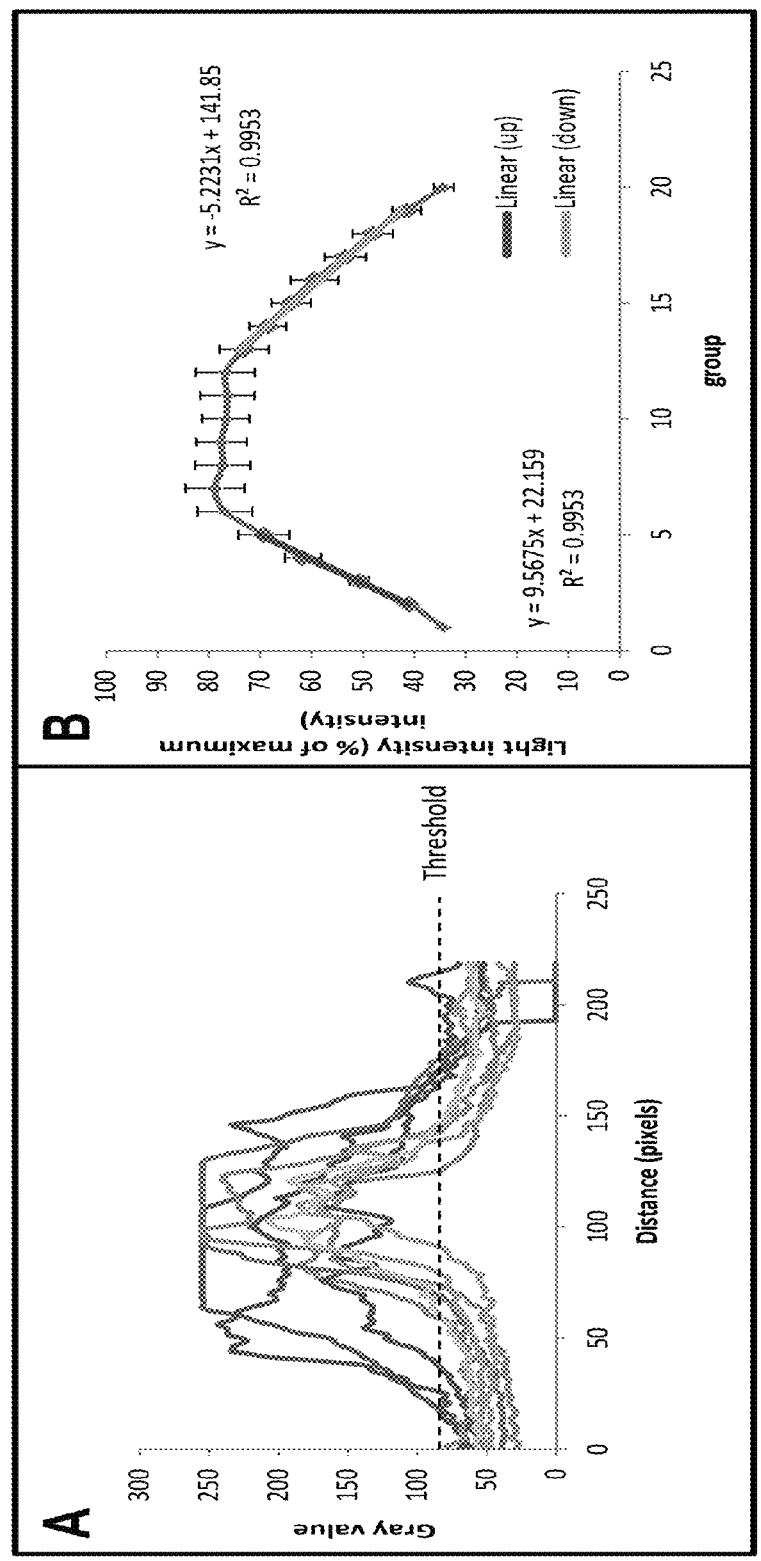
FIGS. 12A-12B illustrate light intensity profile of platelet aggregates. Light intensity profile of nine platelet aggregates of the combined image presented in FIG. 11A were measured (A). A threshold was applied to separate beginning of platelet aggregate from light background, then lengths of aggregates were normalized, and light intensity was reported as percentage of maximum intensity. Average profile of the nine platelet aggregates after normalization is shown in panel (B).

Normalized and averaged light intensity profiles of nine aggregates show an asymmetric aggregate geometry aligned in the direction of the flow. Image analysis shows an abrupt increase in light intensity upstream of the aggregate (linear increase with a slope of 9.6) with a more gradual decrease downstream (linear decrease with a slope of 5.2) (see FIGS. 12A-12B). The apex, or maximal height of each aggregate was typically located at the proximal end of each aggregate (upstream side).

Figure 13:
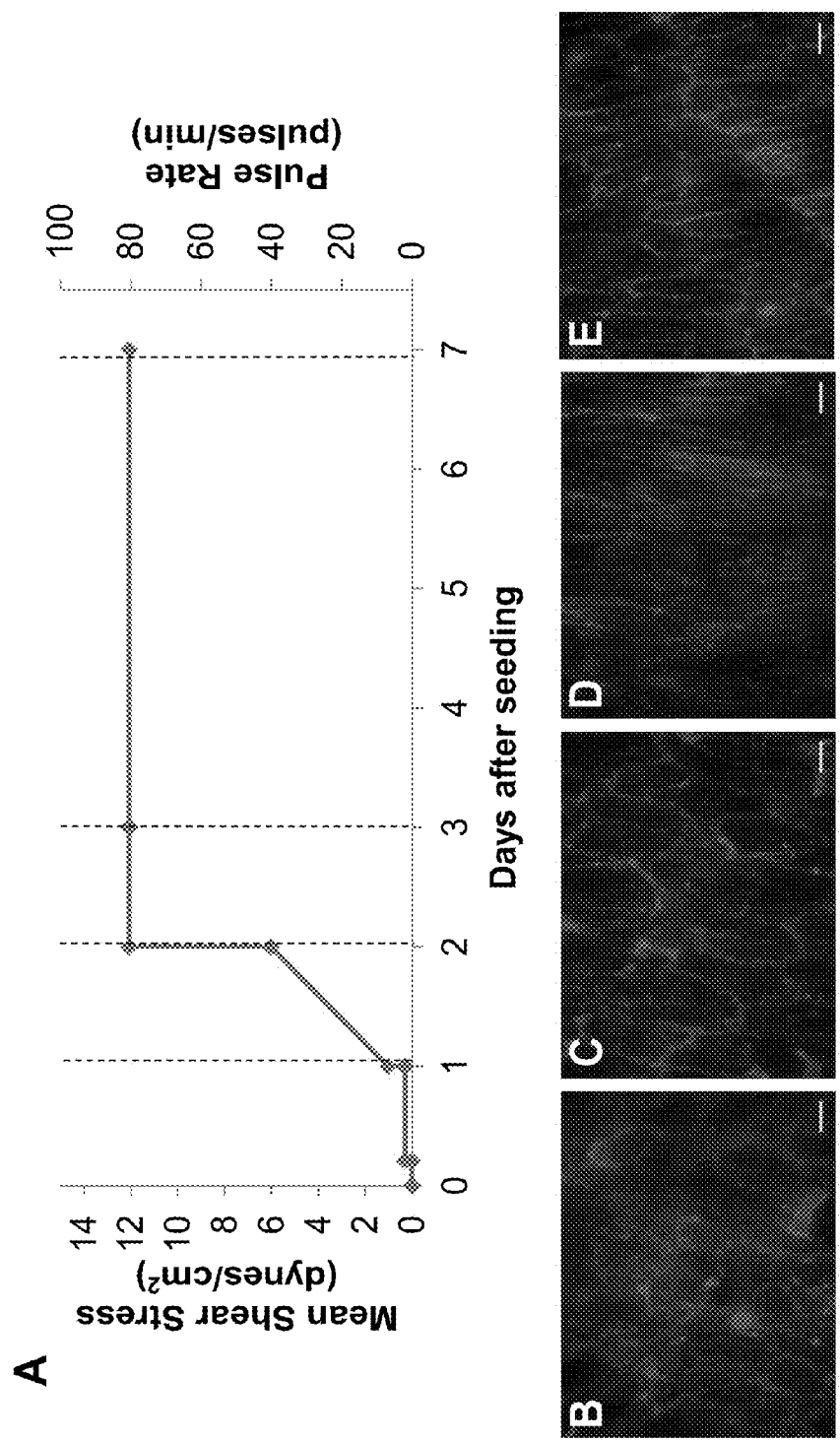
FIGS. 13A-13E illustrate shear conditioning of endothelialized human umbilical vein scaffolds. Decellularized HUV scaffolds were affixed to flow chambers as described. Endothelial cells were seeded onto the lumenal HUV surface at a high concentration and gradually adapted to flow using computer-controlled peristaltic pumps. Panel (A) shows the calculated mean wall shear stress along the lumenal HUV surface over the culture period. At various time points (indicated by the dashed lines), monolayers were fixed and co-stained with rhodamine phalloidin/DAPI to visualize F-actin/cell nuclei, respectively. Panels (B-E) show representative images of endothelial cell morphology at 1, 2, 3, and 7 days after seeding, respectively. Scale bars: 10 μm.

Formation and Shear Conditioning of Neo-Endothelia:

The capacity of the flow chamber to support extended duration perfusion culture of endothelial cells was tested. Specifically, we used the device to assess the potential of the decellularized HUV to support an endothelial cell monolayer under physiological flow conditions. Primary endothelial cells were seeded onto the lumenal surface of the HUV at an initial seeding density of 60,000 cells/cm$^2$, which approximated a nearly confluent density (see FIG. 9B). Seeded cells were then conditioned to shear stress by ramping the flow rate as indicated in FIG. 13A. Two days after seeding, a confluent neo-endothelium had developed that was maintained under continuous pulsatile perfusion with shear stresses commonly found in small-diameter arteries (mean±amplitude 12±12 dynes/cm$^2$ at 80 pulses/min) up to 7 days (FIGS. 13B, 13C). Cytoskeletal F-actin filaments progressively aligned parallel to the flow direction, and nuclear alignment and elongation in the flow direction was also observed over time (see FIGS. 13B-13E).

Figure 14:
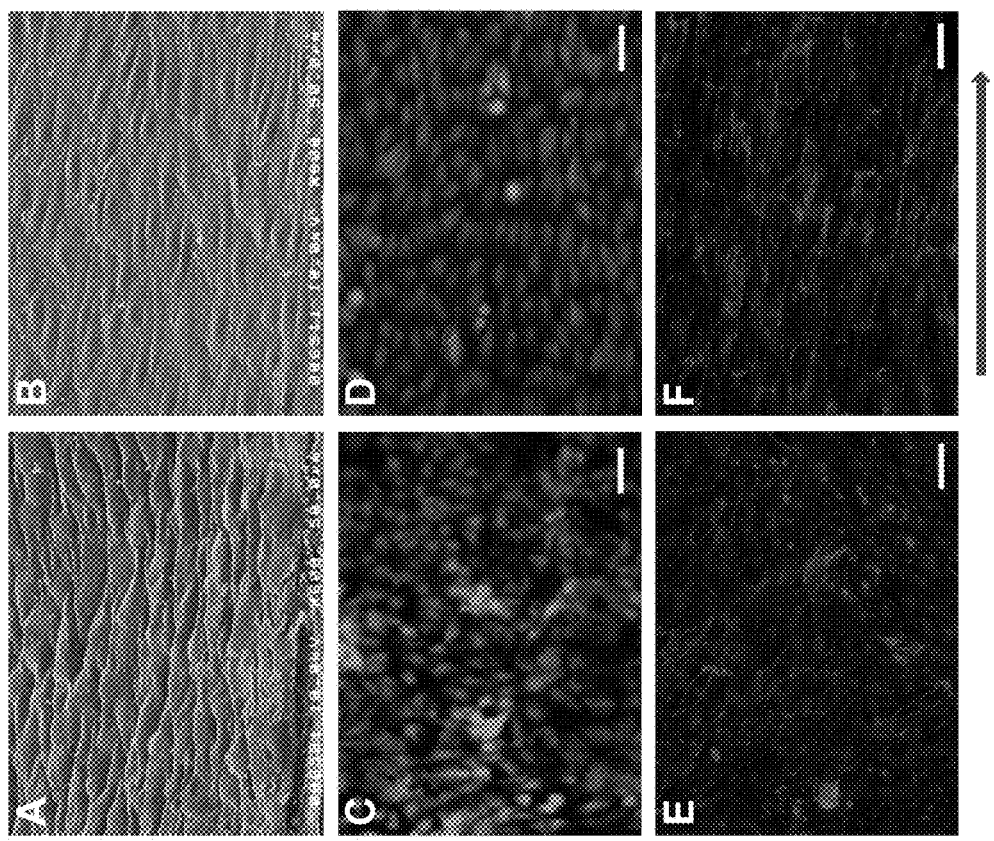
FIGS. 14A-14F illustrate a morphological comparison of endothelia cultured under static culture or flow conditions. Processed human umbilical vein scaffolds were fit in custom-designed flow chambers as described previously. Primary endothelial cell suspensions were injected into the flow field and either cultured under static conditions (A, C, E) or adapted to flow (B, D, F) over a 72 hour period. Scanning electron micrographs of endothelialized HUV scaffolds at oblique angle show the more flattened morphology under flow (B) than under static culture (A). Calcein/ethidium live/dead staining reveal high cellular viability in static culture (C) or under shear stress (D). F-actin/DAPI staining shows cytoskeletal F-actin (red)/cell nuclei (blue) (E, F). Arrow shows the flow direction in B, D, and F. Scale bars represent 50 μm in (A,B) and 25 μm in (C-F).

Morphological Comparison of Endothelia Cultured Under Static Culture or Flow Conditions:

Neo-endothelia cultured on the opaque lumenal surface of decellularized HUV (as described above) were subjected to either pulsatile shear stress (12±12 dynes/cm$^2$ at 80 pulses/min) or static culture conditions for 24 hours. SEM taken from an oblique (45°) angle relative to the HUV surface show endothelial cells cultured under flow to have a significantly more flattened morphology, with less variation in height than static-cultured cells (see FIGS. 14A-14B). This finding correlated with cellular elongation in the flow direction (see FIGS. 14E-14F), which accounts for the reduced topographical variation between cell-cell junctions that is visible in SEM images. Calcein/ethidium co-staining confirmed a high proportion of viable cells on endothelial monolayers cultured on the HUV basement membrane, and exposure to arterial shear stress levels had no deleterious effect on cellular viability (see FIGS. 14C-14D).

Figure 15:
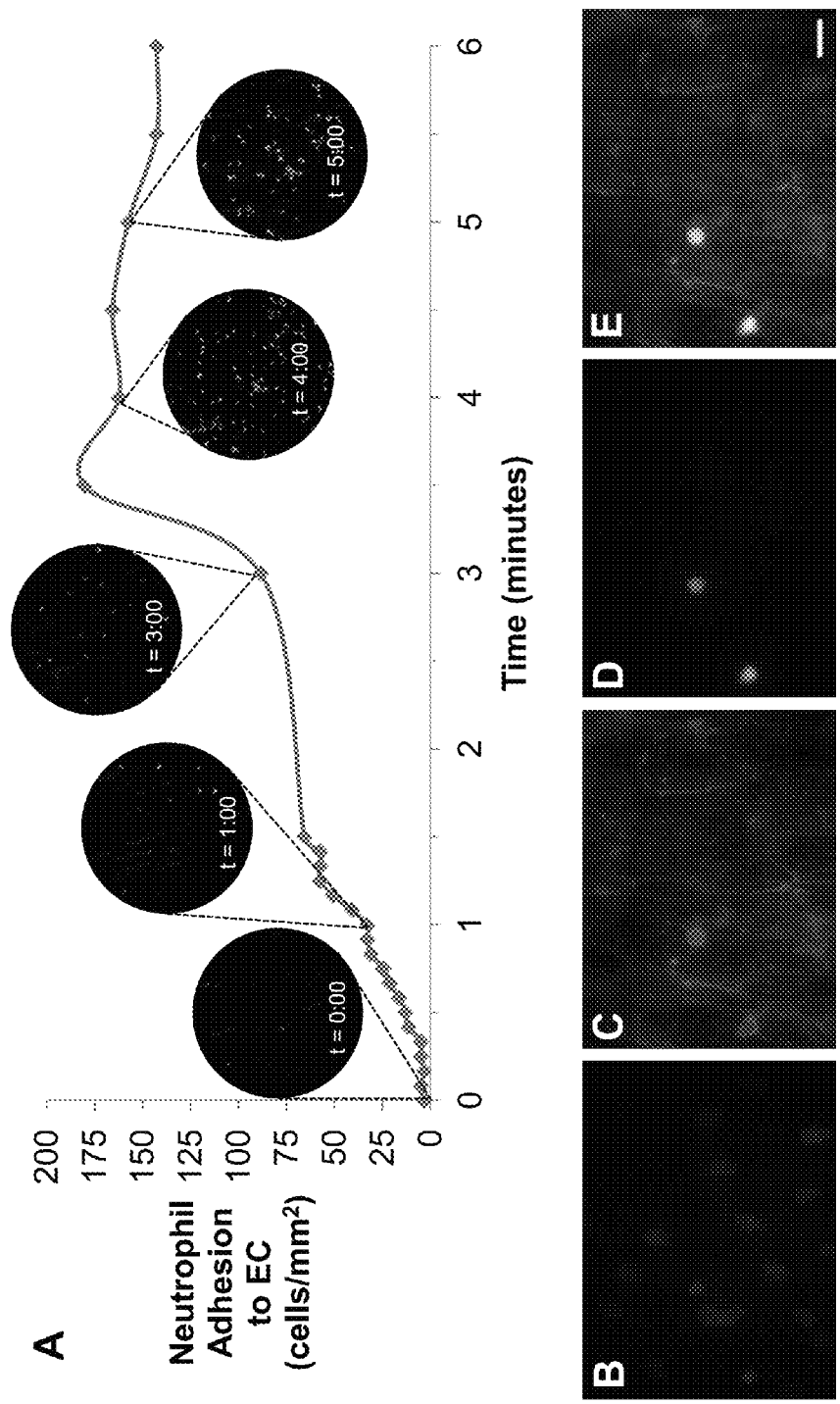
FIGS. 15A-15E illustrate a time lapse capture of neutrophil adhesion to endothelialized HUV scaffolds. Endothelia adapted to flow were activated with 1 U TNF-α. A bolus of neutrophils was then flowed across the lumenal HUV surface at a calculated shear stress of 1 dyne/cm$^2$. Time lapse imaging captured adhesion of GFP+ neutrophils to the activated endothelia over 5 minutes (A). Shown are images at various time points throughout the experiment. After GFP+ neutrophils were flowed across the surface, non-adherent cells were washed away and scaffolds were fixed and co-stained with rhodamine phalloidin/DAPI. Multi-dimensional images show a confluent endothelial monolayer with adherent GFP+ neutrophils (B-E). B: cell nuclei; C: F-actin; D: GFP+ neutrophils; E: overlay. Scale bar: 10 μm.

Real-Time Observation of Neutrophil Rolling on Neo-Endothelia:

For functional assessment of neo-endothelia, we designed a system to image rolling adhesion and arrest of human leukocytes under flow. After 3 days of flow conditioning endothelial cell monolayers were activated with recombinant human TNF-α to stimulate cell adhesion molecule expression. Time lapse imaging conducted at 10× magnification (for observing a larger surface area) captured rolling adhesion and arrest of GFP-expressing neutrophils over a 5 minute period (see FIG. 15A). Quantification of adherent cells in each frame showed a roughly linear increase that reached a plateau after 4 minutes. Rhodamine phalloidin/DAPI co-staining confirmed the presence of a confluent endothelial cell monolayer beneath adherent neutrophils, which predominantly localized at cell-cell junctions (see FIGS. 15B-15E).

Discussion

Several techniques have been developed for visualizing the dynamic events associated with platelet aggregation/leukocyte adhesion both in vivo and in vitro. Intravital microscopy allows real-time observation of leukocyte trafficking to sites of injury, rolling adhesion, and extravasation (Lehr, Leunig et al. 1993; Eriksson, Werr et al. 2000; Zinselmeyer, Lynch et al. 2008) as well as thrombus formation in situ. (Cooley 2011; Kuijpers and Heemskerk 2012) While intravital microscopy is useful for visualizing local cell influx during inflammation, it can only be performed using small animal models due to limited penetration depth of the light source. (Zarbock and Ley 2009)

Other systems have been developed for analyzing vascular behavior ex vivo, where biochemical factors, the mechanical stimuli, and interactions with isolated cell populations can be precisely controlled. (Michell, Andrews et al. 2011) These types of systems are particularly suited for observing agonist-induced contraction/dilation and other whole-vessel responses (Butler, Weinbaum et al. 2000; Bagi, Frangos et al. 2005), but have limitations for observing intimal phenomena due to an increase in light scattering coupled with the loss of resolution associated with thicker, opaque vessels. Alternatively, harvested vessels can be opened longitudinally to directly image cells adhered to the lumenal surface, but this does not permit real-time imaging under controlled flow conditions. (Bolick, Srinivasan et al. 2005)

Parallel plate flow chambers have been used for several decades to study behavior of particular cell populations under flow. (Frangos, Eskin et al. 1985) These devices have several advantages over tubular ex vivo-derived or engineered vessels: lower reagent requirements, more predictable shear stresses, and non-invasive observation with enhanced clarity compared to intravital microscopy. In most parallel plate designs, a vacuum channel is incorporated to pull a glass slide over a gasket of known thickness in order to seal the flow channel; for this reason, the substrate must be rigid. (Frangos, Eskin et al. 1985; Reinhart-King, Fujiwara et al. 2008) The use of glass/polystyrene substrates in these systems has become a limiting factor as the dynamics of cell adhesion are significantly influenced by the physical properties of the underlying culture substrate (e.g. surface modulus, topography), which affects the way cells attach, spread, and adapt to fluid forces. (Gray, Tien et al. 2003; Ingber 2010) Given the disparities in the physical properties of extracellular matrix proteins of blood vessels and tissue culture plastics, the use of these materials for studying cell behavior under flow may be less than ideal.

To overcome the limitations associated with imaging through thick, opaque vessels, we designed a novel flow chamber that holds a compliant vascular biomaterial in a predetermined conformation such that shear stress across the wall can be precisely controlled. By cutting a vessel open longitudinally and securing it between two plates, the intimal surface can be visualized while whole blood, select cell suspensions, or media with agonists are perfused across. This permits live imaging using conventional epifluorescence microscopy techniques. In the current study, the human umbilical vein (HUV) was used as a naturally-derived model blood vessel. The HUV has been used in vascular reconstruction surgeries for over 30 years (Dardik 2006), and has previously been developed as an ex vivo-derived, acellular vascular scaffold. (Daniel, Abe et al. 2005; Tosun, Villegas-Montoya et al. 2011) Due to its clinical relevance, the HUV served as an excellent model to assess a natural vascular substrate for both re-endothelialization as well as modeling platelet/neutrophil adhesion under flow.

Platelet adhesion/aggregation to vascular graft surfaces is directly related to the propensity of these materials to adsorb plasma proteins. (Hu, Eaton et al. 2001) Deposition of plasma proteins varies depending on the hydrophilicity, surface charge, and chain mobility; it is the combination of these factors that determines the thrombogenicity of a material and makes prediction difficult. Direct observation and quantification of blood cell adhesion onto clinically relevant materials significantly advances our ability to predict thrombotic responses. Also, as the complexity of the basement membrane is difficult to reproduce in vitro, the study of platelet aggregation under flow has previously been limited to single protein types. (Colace, Falls et al. 2011) Using this design we were able to observed aggregate formation directly on a complex subendothelial basement membrane providing a more comprehensive perspective on adhesion events.

Platelet adhesion to proteins is highly dependent on global shear trends and local microgradients created by thrombi formation that also influence aggregate morphology. (Nesbitt, Westein et al. 2009) The capacity to create real-time light intensity profiles allows for the observation and estimation of platelet aggregate geometry (in the z direction). Real-time observations show the aggregates to have a steep height increase upstream with a more gradual decrease downstream. This has previously only been observed as a terminal analysis without the capacity to assess progressive changes (Tolouei, Butler et al. 2011).

The specific protein composition of the vascular basement membrane regulates endothelial cell phenotype via extracellular matrix-mediated integrin signaling. (Davis and Senger 2005) It has been previously shown that sub-endothelial protein substrates influence activation of signaling pathways elicited by shear stress. (Orr, Sanders et al. 2005; Hahn, Orr et al. 2009) The use of a natural basement membrane may therefore serve as a more physiologically relevant substrate for modeling hemodynamic shear stress patterns in vitro. In the present study, we were able to temporally observe endothelial cell proliferation and morphological adaptation to shear stress applied in situ. To avoid stripping endothelial cells off the HUV surface by the sudden onset of flow, cells were shear conditioned by progressively increasing flow rates until physiological levels of arterial wall shear stress were reached. Adaptation of EC on other vascular biomaterials to physiological shear levels could similarly be optimized using this device in preparation for implantation in the aggressive arterial circulation. In summary, we have designed and characterized a novel flow chamber that uses ex vivo-derived vascular tissues for in vitro modeling of cell adhesion events in an environment more reminiscent of the natural vasculature. We have demonstrated functional uses of this device for investigating cell adhesion events during normal vascular homeostasis or in response to injury. The design presented can be used for pre-implantation screening of a wide range of other biomaterials to assess blood cell interactions.

References, each of which is incorporated herein by reference

Bacabac, R. G., T. H. Smit, et al. (2005). "Dynamic shear stress in parallel-plate flow chambers." J Biomech 38(1): 159-167.

Bagi, Z., J. A. Frangos, et al. (2005). "PECAM-1 mediates NO-dependent dilation of arterioles to high temporal gradients of shear stress." Arterioscler Thromb Vasc Biol 25(8): 1590-1595.

Barthel, K. U. (2011). Interactive 3D Surface Plot v2.33 plug-in for ImageJ, Internationale Medieninformatik.

Bolick, D. T., S. Srinivasan, et al. (2005). "Sphingosine-1-phosphate prevents tumor necrosis factor-{alpha}-mediated monocyte adhesion to aortic endothelium in mice." Arterioscler Thromb Vasc Biol 25(5): 976-981.

Butler, P. J., S. Weinbaum, et al. (2000). "Endothelium-dependent, shear-induced vasodilation is rate-sensitive." Microcirculation 7(1): 53-65.

Colace, T., E. Falls, et al. (2011). "Analysis of morphology of platelet aggregates formed on collagen under laminar blood flow." Ann Biomed Eng 39(2): 922-929.

Cooley, B. C. (2011). "In vivo fluorescence imaging of large-vessel thrombosis in mice." Arterioscler Thromb Vasc Biol 31(6): 1351-1356.

Daniel, J., K. Abe, et al. (2005). "Development of the human umbilical vein scaffold for cardiovascular tissue engineering applications." ASAIO J 51(3): 252-261.

Dardik, H. (2006). "A 30-year odyssey with the umbilical vein graft." J Am Coll Surg 203(4): 582-583.

Davis, G. E. and D. R. Senger (2005). "Endothelial extracellular matrix: biosynthesis, remodeling, and functions during vascular morphogenesis and neovessel stabilization." Circ Res 97(11): 1093-1107.

de Mel, A., G. Jell, et al. (2008). "Biofunctionalization of biomaterials for accelerated in situ endothelialization: a review." Biomacromolecules 9(11): 2969-2979.

Eriksson, E. E., J. Werr, et al. (2000). "Direct observations in vivo on the role of endothelial selectins and alpha(4) integrin in cytokine-induced leukocyte-endothelium interactions in the mouse aorta." Circ Res 86(5): 526-533.

Frangos, J. A., S. G. Eskin, et al. (1985). "Flow effects on prostacyclin production by cultured human endothelial cells." Science 227(4693): 1477-1479.

Frangos, J. A., L. V. McIntire, et al. (1988). "Shear stress induced stimulation of mammalian cell metabolism." Biotechnol Bioeng 32(8): 1053-1060.

Gray, D. S., J. Tien, et al. (2003). "Repositioning of cells by mechanotaxis on surfaces with micropatterned Young's modulus." J Biomed Mater Res A 66(3): 605-614.

Hahn, C., A. W. Orr, et al. (2009). "The subendothelial extracellular matrix modulates JNK activation by flow." Circ Res 104(8): 995-1003.

Hu, W. J., J. W. Eaton, et al. (2001). "Molecular basis of biomaterial-mediated foreign body reactions." Blood 98(4): 1231-1238.

Ingber, D. E. (2010). "From cellular mechanotransduction to biologically inspired engineering: 2009 Pritzker Award Lecture, BMES Annual Meeting Oct. 10, 2009." Ann Biomed Eng 38(3): 1148-1161.

Jaffe, E. A., R. L. Nachman, et al. (1973). "Culture of human endothelial cells derived from umbilical veins. Identification by morphologic and immunologic criteria." J Clin Invest 52(11): 2745-2756.

Kannan, R. Y., H. J. Salacinski, et al. (2005). "Current status of prosthetic bypass grafts: a review." J Biomed Mater Res B Appl Biomater 74(1): 570-581.

Kapadia, M. R., D. A. Popowich, et al. (2008). "Modified prosthetic vascular conduits." Circulation 117(14): 1873-1882.

Kuijpers, M. J. and J. W. Heemskerk (2012). "Intravital imaging of thrombus formation in small and large mouse arteries: experimentally induced vascular damage and plaque rupture in vivo." Methods Mol Biol 788: 3-19.

L'Heureux, N., N. Dusserre, et al. (2006). "Human tissue-engineered blood vessels for adult arterial revascularization." Nat Med 12(3): 361-365.

Lehr, H. A., M. Leunig, et al. (1993). "Dorsal skinfold chamber technique for intravital microscopy in nude mice." Am J Pathol 143(4): 1055-1062.

Mehta, D., M. B. Izzat, et al. (1997). "Towards the prevention of vein graft failure." Int J Cardiol 62 Suppl 1: S55-63.

Michell, D. L., K. L. Andrews, et al. (2011). "Imaging leukocyte adhesion to the vascular endothelium at high intraluminal pressure." J Vis Exp(54).

Mollinedo, F., R. López-Pérez, et al. (2008). "Differential gene expression patterns coupled to commitment and acquisition of phenotypic hallmarks during neutrophil differentiation of human leukaemia HL-60 cells." Gene 419(1-2): 16-26.

Nesbitt, W. S., E. Westein, et al. (2009). "A shear gradient-dependent platelet aggregation mechanism drives thrombus formation." Nat Med 15(6): 665-673.

Orr, A. W., J. M. Sanders, et al. (2005). "The subendothelial extracellular matrix modulates NF-kappaB activation by flow: a potential role in atherosclerosis." J Cell Biol 169(1): 191-202.

Reinhart-King, C. A., K. Fujiwara, et al. (2008). "Physiologic stress-mediated signaling in the endothelium." Methods Enzymol 443: 25-44.

Sarkar, S., K. M. Sales, et al. (2007). "Addressing thrombogenicity in vascular graft construction." J Biomed Mater Res B Appl Biomater 82(1): 100-108.

Schmidtke, D. W. and S. L. Diamond (2000). "Direct observation of membrane tethers formed during neutrophil attachment to platelets or P-selectin under physiological flow." J Cell Biol 149(3): 719-730.

Tolouei, E., C. J. Butler, et al. (2011). "Effect of hemodynamic forces on platelet aggregation geometry." Ann Biomed Eng 39(5): 1403-1413.

Tosun, Z., C. Villegas-Montoya, et al. (2011). "The influence of early-phase remodeling events on the biomechanical properties of engineered vascular tissues." J Vasc Surg 54(5): 1451-1460.

Yazdani, S. K., B. W. Tillman, et al. (2010). "The fate of an endothelium layer after preconditioning." J Vasc Surg 51(1): 174-183.

Zarbock, A. and K. Ley (2009). "New insights into leukocyte recruitment by intravital microscopy." Curr Top Microbiol Immunol 334: 129-152.

Zinselmeyer, B. H., J. N. Lynch, et al. (2008). "Video-rate two-photon imaging of mouse footpad—a promising model for studying leukocyte recruitment dynamics during inflammation." Inflamm Res 57(3): 93-96.

Example 3

Introduction:

Coronary heart disease (CHD) accounted for 425,425 deaths in the United States in 2006. For patients with CHD, a bypass of coronary arteries can be performed to improve blood circulation. This surgical procedure requires small diameter grafts with adequate mechanical strength, and blood compatibility. The limited supply of suitable small diameter grafts has led to the development of tissue engineered blood vessel substitutes. While a large body of work exists that describes blood cell adhesion onto modified glass and/or translucent materials, studies of cell adhesion to a complex basement membrane has been limited due to restraints in observing adhesion to opaque materials. In these investigations a flow chamber has been designed to observe in real time blood—basement membrane interactions. Using the human umbilical vein (HUV) as a model system, human platelet interactions with this graft have been assessed first under static and then flow conditions.

Figure 16:
FIG. 16 illustrates an embodiment of a flow chamber.
Figure 17:
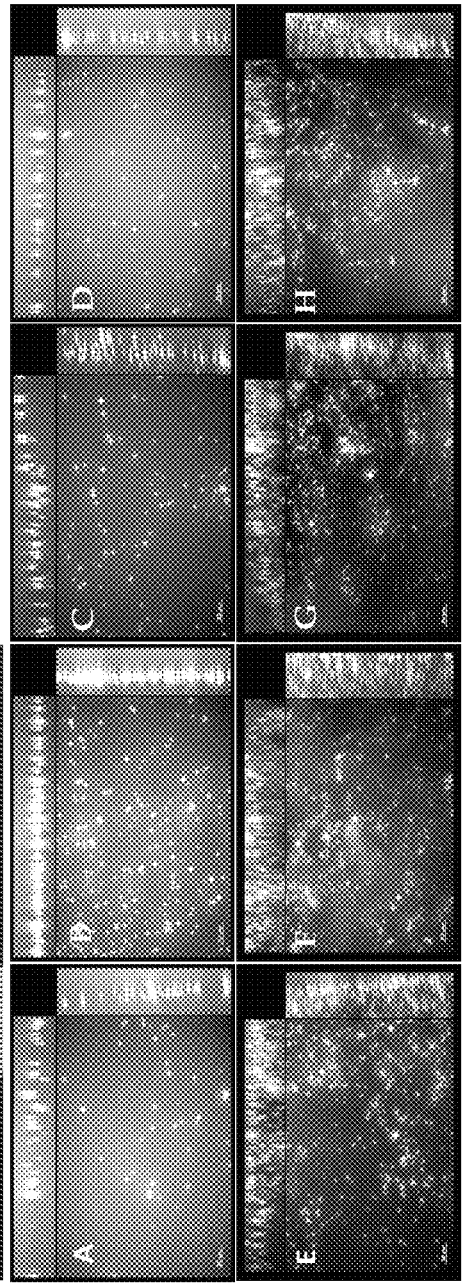
FIGS. 17A-17H illustrate an embodiment of a platelet layout (A-H) of highly scattered on the ablumen of the HUV and more regular on the lumen.

Methods:

HUV were extracted from umbilical cords freshly collected from Shands hospital, Gainesville Fla. via an automated lathing technique. Veins were decellularized using either 2M NaCl, a solution made of ethanol, acetone, and H2O (EtAc—60:20:20 ratio), 1% Triton X-100, or 1% sodium dodecyl sulfate (SDS). Cellular veins were also crosslinked with 3% glutaraldehyde (Glu3%) to assess grafts currently used in the clinic. Human venous blood was collected from normal healthy adult volunteers. Platelets were fluorescently labeled. Platelets were or incubated with HUV for 2 hours (static experiments), or flowed on the lumen side of the HUV using a newly developed acrylic flow chamber designed to replicate earlier parallel plate geometries. HUV was fixed to geometries. HUV was fixed to the lower surface of the chamber and adhesion was observed via a window located on the top plate (FIG. 16).

Results:

Platelet Adhesion to Decellularized HUV in Static Conditions

Figure 18:
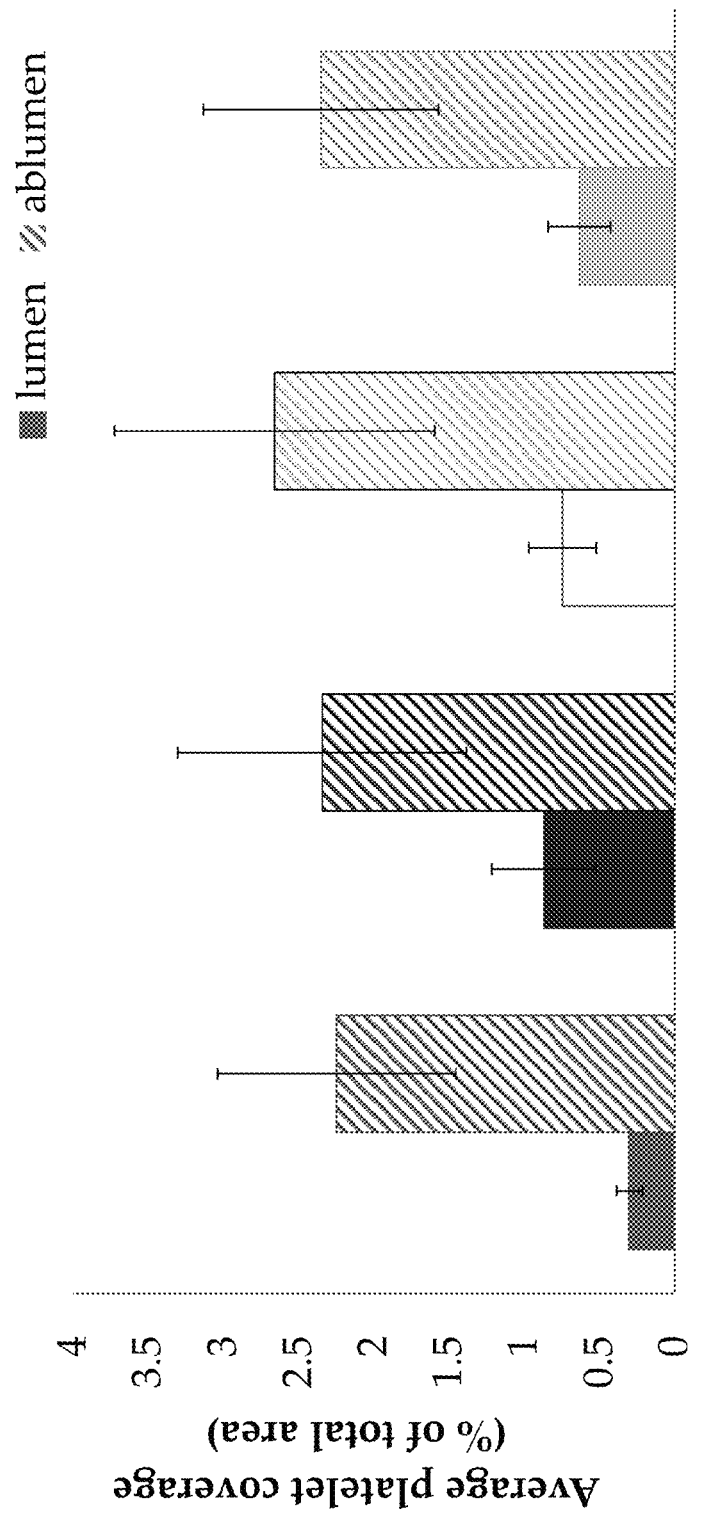
FIG. 18 illustrates the effect of decellularization treatment on platelet adhesion of HUV. (*, p<0.05 vs. Each decellularization method, ** p<0.05 vs. lumen for same decellularization method, Student t-test; n=4).
Figure 19:
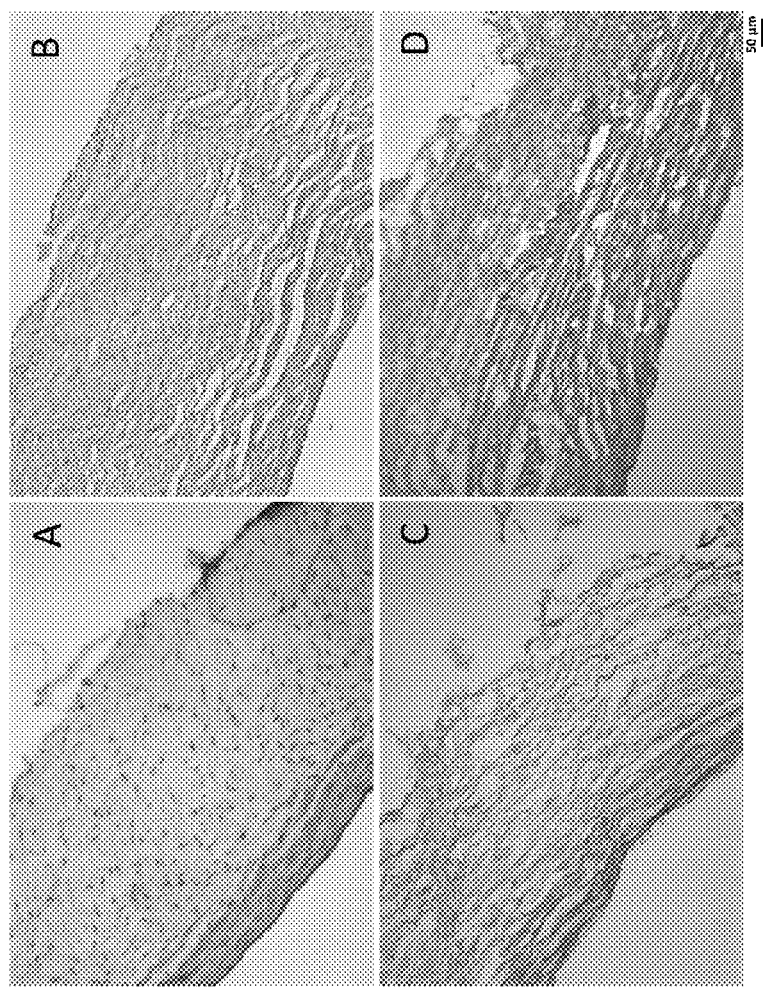
FIGS. 19A-19D illustrate H&E staining of (A) Native, (B) crosslinked with gluteraldehyde, (C) SDS treated, and (D) EtAc treated HUV.

Platelet layout is highly scattered on the ablumen of the HUV and more regular on the lumen (FIGS. 17A-17G). While platelets seem to preferentially adhere to the ablumen, decellularization treatment has a limited influence on amount of adhesion (FIG. 18).

Significant difference in adhesion was observed between SDS and EtAc. These treatments being respectively the most commonly used for scaffold decellularization and the one leading to the least platelet adhesion, their effect on platelet/HUV interactions was then assessed under flow conditions.

Processing the HUV via decellularization as well as glutaraldehyde cross-linking influenced its structure. Both treatment types induced partial alteration of the extracellular matrix (FIGS. 19A-19D).

Figure 20:
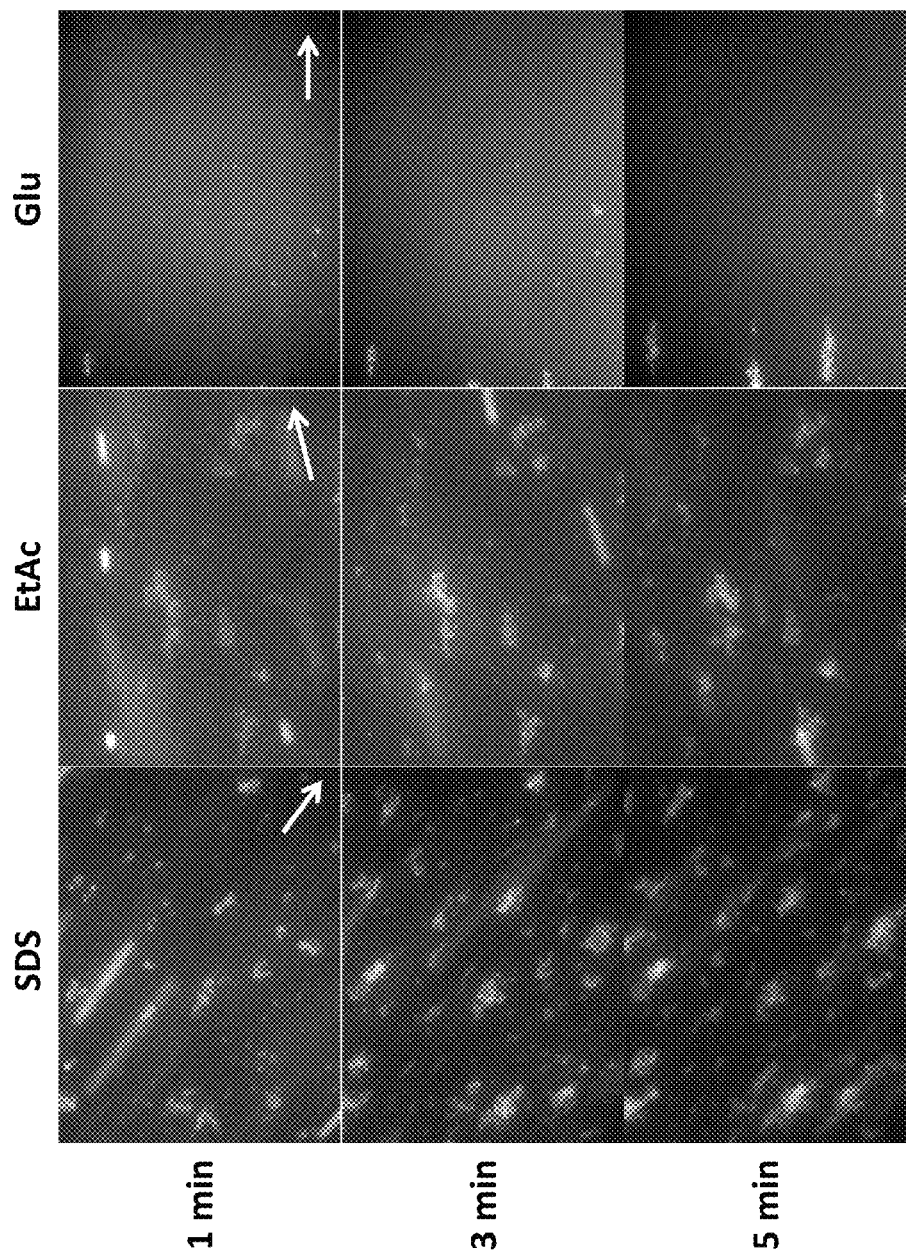
FIG. 20 illustrates representative fluorescent images of platelets adhesion to lumen of processed HUV, overtime, under a shear rate of 600 s$^{-1}$+/−100. White arrows represent flow direction.

While in static conditions platelets tend to adhere to the HUV individually, under flow conditions they seemed to form aggregates (FIG. 20).

Figure 21:
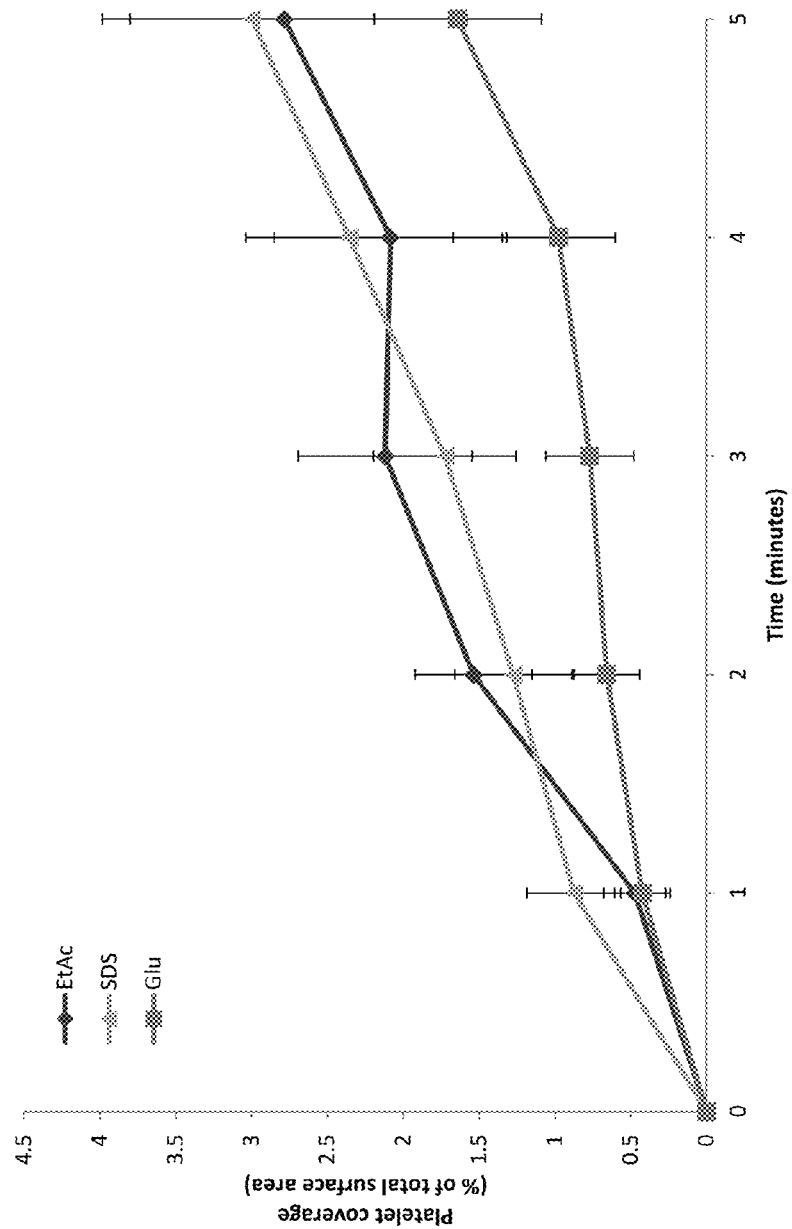
FIG. 21 illustrates a graph showing the influence of HUV treatment on platelet adhesion under flow (shear rate of 600 s$^{-1}$+/−100).

Within arterial range flow rate, glutaraldehyde crosslinking of the HUV limited platelet adhesion more efficiently than decellularization treatment (FIG. 21).

CONCLUSIONS

Platelet interactions with a surface are influenced by the morphology and chemical characteristics of this one. Difference of adhesion shown between lumen and ablumen of the HUV is certainly linked to a difference of surface morphology. The albumen surface is constituted of mucous tissue which has been disrupted along HUV processing, leading to a rough surface in which platelets can be confined. For static and dynamic experiments, a same trend was observed: platelets adhesion was higher for SDS than EtAc treated grafts. It has previously been shown that decellularization treatments alter the structure of biological scaffolds, for example SDS damages collagen fibers while EtAc crosslinks these same fibers. These structure modifications must affect platelet/scaffold interactions. Glutaraldehyde is a crosslinker which blocks irreversibly the epitopes located at the surface and reduce platelet accessibility. Also, it has previously been observed that implanted biomaterials rapidly acquire a layer of host proteins on which platelets tend to adhere. The deposited layer of plasma proteins varies depending on the hydrophilicity, surface charge, and chain mobility of the biomaterial. Glutaradehyde crosslinking may reduce plasma protein deposition, and so reduce platelet binding.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of the numerical value, or more of the numerical value(s) being modified.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A device comprising:
a first plate and a second plate defining a flow chamber between the plates, the first plate configured to hold an independent substrate comprising a sample and comprising a securing structure for securing the substrate within the flow chamber, and the second plate comprising an integrated, recessed, optically transparent viewing window, a top surface of the viewing window being recessed below a top surface of the second plate and defining a recessed area in the second plate, and a bottom surface of the viewing window forming a portion of the flow chamber adjacent the sample to allow viewing of the sample through the viewing window;
a first inlet port at a first end of the device that is configured to flow a first fluid;
a flow channel within the flow chamber defined in part by the second plate and in part by the first plate, the substrate, or both, wherein the flow channel is in fluidic communication with the first inlet port and is configured so the first fluid contacts a side of the sample adjacent the viewing window and the sample is viewed through the optically transparent viewing window in real time as the sample is exposed to the first fluid;
and an exit port that is in fluidic communication with the flow channel, wherein the flow channel is configured so that the first fluid flows from the first inlet port side to the exit port side of the flow channel.

2. The device of claim 1, wherein the flow channel has a length of about 5 mm to 250 mm, a width of about 1 mm to 50 mm, and a height of about 25 µm to 10 mm.

3. The device of claim 1, wherein the flow channel is configured so that the first fluid contacts both sides of the substrate.

4. The device of claim 1, wherein the flow channel is configured so that the substrate defines one surface of the flow channel and the second plate defines a second surface of the flow channel and the first fluid contacts the side of the substrate adjacent the viewing window.

5. The device of claim 1, wherein the securing structure includes a groove in the first plate that secures the substrate within the flow chamber.

6. The device of claim 5, further comprising a second securing structure to secure the substrate to the groove, wherein the second securing structure is positioned on the side of the substrate opposite of the groove.

7. The device of claim 6, wherein the second securing structure is a gasket configured to fit within the groove to secure a portion of the substrate within the groove.

8. The device of claim 1, wherein the substrate comprises a flexible scaffold material including a plurality of cells.

9. The device of claim 1, further comprising: a second inlet port at the first end of the device that is configured to flow a second fluid; wherein the flow channel is in fluidic communication with the second inlet port, wherein the flow channel is configured so the second fluid contacts a side of the sample.

10. The device of claim 9, wherein the flow channel is configured so that the second fluid contacts both sides of the sample.

11. The device of claim 9, wherein the flow channel is configured so that the second fluid contacts one side of the sample opposite the side of the sample contacted by the first fluid.

12. The device of claim 9, further comprising an optically transparent second viewing window in the first plate disposed adjacent the flow channel on the side opposite the viewing window to view the sample in real time as the sample is exposed to the second fluid.

13. The, device of claim 1, wherein the recessed, optically transparent viewing window is configured to allow positioning an objective of a microscope within the recessed area adjacent the top surface of the optically transparent viewing window to view the sample under magnification.

14. The device of claim 13, wherein the microscope objective is positioned about 25 µm to 10 mm from the sample.

15. The device of claim 13, wherein the optically transparent viewing window has a thickness adapted to allow imaging of the sample with a microscope under magnification of about 40× or greater.

16. The device of claim 1, wherein the substrate is opaque.

17. The device of claim 1, wherein the substrate has a thickness between 0.5 and 1.5 mm.

18. A flow chamber assembly comprising:
a base plate configured to hold a substrate comprising a sample, the base plate comprising a securing structure for securing the substrate within the flow chamber; and
a flow chamber plate configured to fit over the base plate, such that a first flow channel is defined by the base plate, substrate, and flow chamber plate, the flow chamber plate comprising:
a top surface;
a bottom surface configured to secure to the base plate;
a first inlet port at a first end of the flow chamber plate that is in fluidic communication with the flow channel and is configured to flow a first fluid such that the first fluid contacts a first surface of the substrate facing the flow chamber plate;
an exit port at a second end of the device that is in fluidic communication with the flow channel and is also configured to flow a first fluid; and
an optically transparent viewing window comprising a transparent material having a lower surface defining a portion of the flow channel above the substrate and having an upper surface recessed below the top surface of the flow chamber plate, wherein the optically transparent viewing window is configured to allow viewing of the substrate through the transparent material,
wherein the flow chamber plate is configured so that the first fluid flows from the first inlet port side, through the flow channel where it contacts the first surface of the substrate, to the exit port side of the flow channel, such that the substrate is viewed in real time as the substrate is exposed to the first fluid.

19. The device of claim 18, wherein the securing structure on the base plate comprises a groove in the base plate for securing the substrate within the flow chamber, and wherein the device further comprises a gasket positioned on a side of the substrate opposite of the groove and configured to fit within the groove, wherein the gasket secures a portion of the substrate within the groove.

20. The device of claim 18, wherein the substrate comprises a compliant vascular biomaterial.

* * * * *